(12) United States Patent
Takegawa et al.

(10) Patent No.: US 7,449,466 B2
(45) Date of Patent: Nov. 11, 2008

(54) CYCLIC AMINOPHENYL SULFAMATE DERIVATIVE

(75) Inventors: Shigehiro Takegawa, Kawasaki (JP);
Shigeki Iwashita, Kawasaki (JP);
Makoto Okada, Kawasaki (JP);
Takayoshi Nakagawa, Fujisawa (JP);
Naoyuki Koizumi, Sagamihara (JP);
Tomohito Fujii, Kawasaki (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 219 days.

(21) Appl. No.: 10/558,253

(22) PCT Filed: May 7, 2004

(86) PCT No.: PCT/JP2004/006490

§ 371 (c)(1),
(2), (4) Date: Nov. 21, 2005

(87) PCT Pub. No.: WO2004/103971

PCT Pub. Date: Dec. 2, 2004

(65) Prior Publication Data

US 2006/0189625 A1    Aug. 24, 2006

(30) Foreign Application Priority Data

May 21, 2003    (JP) .............................. 2003-143503

(51) Int. Cl.
| A61K 31/497 | (2006.01) |
| A61K 31/4965 | (2006.01) |
| A61K 31/445 | (2006.01) |
| A01N 43/40 | (2006.01) |
| C07D 401/00 | (2006.01) |
| C07D 241/04 | (2006.01) |
| C07D 295/00 | (2006.01) |
| C07D 211/40 | (2006.01) |
| C07D 211/54 | (2006.01) |

(52) U.S. Cl. .............................. 514/253.01; 514/255.02; 514/255.03; 514/317; 544/360; 544/396; 546/216

(58) Field of Classification Search ........................ None
See application file for complete search history.

(56) References Cited

U.S. PATENT DOCUMENTS 3,082,238 A * 3/1963 Dunbar ........................ 558/47

| 5,616,574 A | 4/1997 | Reed et al. |
| 5,830,886 A | 11/1998 | Reed et al. |
| 6,011,024 A | 1/2000 | Reed et al. |
| 6,159,960 A | 12/2000 | Reed et al. |
| 6,187,766 B1 | 2/2001 | Reed et al. |
| 6,476,011 B1 | 11/2002 | Reed et al. |
| 6,642,397 B1 | 11/2003 | Reed et al. |
| 6,677,325 B2 | 1/2004 | Reed et al. |
| 6,762,205 B1 | 7/2004 | Koizumi et al. |

FOREIGN PATENT DOCUMENTS

| WO | 93/05064 | 3/1993 |
| WO | 01/02349 | 1/2001 |
| WO | 03/031397 | 4/2003 |

OTHER PUBLICATIONS

Nicola M. Howarth et al., "Estrone Sulfamates: Potent Inhibitors of Estrone Sulfatase with Therapeutic Potential", J. Med. Chem., 37, pp. 219-221, 1994.

L.W. Lawrence Woo et al., "Active Site Directed Inhibition of Estrone Sulfatase by Nonsteroidal Coumarin Sulfamates", J. Med. Chem., 39, pp. 1349-1351, 1996.

* cited by examiner

*Primary Examiner*—James O. Wilson
*Assistant Examiner*—Jeffrey H Murray
(74) *Attorney, Agent, or Firm*—Wenderoth, Lind & Ponack, L.L.P.

(57) ABSTRACT

This invention provides cyclicamino-phenyl sulfamate derivatives represented by a formula

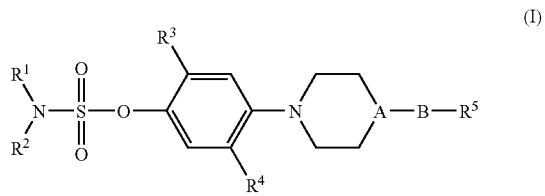

(I)

wherein each of $R^1$ and $R^2$ stands for hydrogen or lower alkyl; each of $R^3$ and $R^4$ stands for hydrogen, halogen, cyano or the like; A stands for nitrogen or CH; B stands for $CH_2$, $SO_2$, CO, optionally substituted phenyl or the like; and $R^5$ stands for alkyl, phenyl, amino or the like, or salts thereof which exhibit excellent steroid sulfatase inhibitory activity and are useful for prevention or treatment of diseases associated with steroids such as estrogen, androgen and the like.

24 Claims, No Drawings

CYCLIC AMINOPHENYL SULFAMATE DERIVATIVE

TECHNICAL FIELD

This invention relates to novel cyclicamino-phenyl sulfamate derivatives or salts thereof, which exhibit excellent steroid sulfatase inhibitory activity and, therefore, are useful for prevention or treatment of diseases associated with steroids such as estrogen, androgen and the like.

BACKGROUND ART

Sulfates of steroids, for example, dehydroepiandrosterone sulfate, cholesterol sulfate, estrone sulfate and the like are intermediate metabolites of steroid within the human body. These sulfates are metabolized into still other steroids in living body. For example, estrone sulfate is hydrolyzed with steroid sulfatase which is present in living body into free estrone which is further reversibly converted to estradiol, with 17β-hydroxysteroid dehydrogenase. These estrogens such as estrone, estradiol and the like which are formed through steroid metabolism are closely associated with such diseases as breast cancer, uterine cancer, ovarian cancer, endometriosis, adenomyosis uteri, mastopathy and the like.

Therefore, effective inhibition of steroid sulfatase activity is expected to be useful for therapy of diseases associated with steroids such as estrogen or androgen, and in line with this concept a number of steroidal compounds which exhibit steroid sulfatase-inhibitory activity, represented by estrone-3-sulfamate (EMATE) have been proposed (cf. PCT International Publication WO 93/05064 Pamphlet).

However, EMATE is a compound inadequate as a therapeutic agent for estrogen-related diseases, because it exhibits also potent estrogenic activity concurrently with potent steroid sulfatase inhibiting activity.

As non-steroidal compounds having steroid sulfatase inhibiting activity, furthermore, a certain kind of coumarin derivatives, e.g., 4-methylcoumarin-7-sulfamate (COUMATE) (cf J. Med. Chem., Vol. 37, 219 (1994)) and a certain kind of phenyl sulfamate derivatives, e.g., 4-(2-myristoylaminoethyl)phenyl sulfamate (DU-14) have been proposed (cf. J. Med. Chem., Vol. 39, 1349 (1996)).

However, these non-steroidal compounds such as COUMATE or DU-14 exhibit low level of steroid sulfatase inhibiting activity which is the main activity, although they are free from estrogenic activity as a side action, and are not yet quite satisfactory.

The present inventors have recently proposed a certain kind of substituted biphenyl sulfamate derivatives which exhibit potent steroid sulfatase inhibiting activity and yet show no estrogenic activity (cf. PCT International publication WO 01/02349 Pamphlet), but have now found that many of these biphenyl type sulfamate derivatives have genetic toxicity.

We have further pursued our research concentratively to now discover that novel cyclicamino-phenyl sulfamate derivatives or salts thereof in which 4-position of the phenyl group is substituted with a cyclic amino group, i.e., piperidinyl group or piperazinyl group, exhibit excellent steroid sulfatase inhibiting activity and yet are free of estrogenic activity and genetic toxicity. The present invention is whereupon completed.

DISCLOSURE OF THE INVENTION

Thus, the present invention provides cyclicamino-phenyl sulfamate derivatives or salts thereof represented by the following formula:

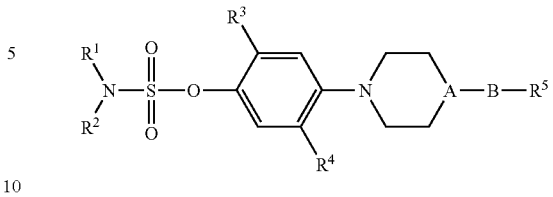

(I)

wherein $R^1$ and $R^2$ stand for, independently from each other, hydrogen or lower alkyl, $R^3$ and $R^4$ stand for, independently from each other, hydrogen, halogen, cyano or lower alkyl, A stands for nitrogen or CH, B stands for $CH_2$, $SO_2$, CO, CH=CH or substituted or unsubstituted phenylene, and $R^5$ stands for hydrogen, straight chain or branched chain $C_1$-$C_{10}$ alkyl, phenyl-lower alkyl (in which the phenyl moiety may be further substituted), benzoyl-lower alkyl (in which the phenyl moiety in the benzoyl may be further substituted), cycloalkyl-lower alkyl, piperidinyl-lower alkyl, substituted or unsubstituted phenyl, substituted or unsubstituted benzoyl or amino (in which the amino may be further substituted with lower alkyl or may form cyclic amino group) or salts thereof.

Hereinafter the present invention is explained in further details.

In the present invention, the term, "lower" signifies the group or compound named with the prefix contains no more than six, preferably no more than four, carbon atoms. Therefore, as examples of "lower alkyl", methyl, ethyl, n-propyl, isopropyl, n-butyl, isobutyl, sec-butyl, tert-butyl, n-pentyl, n-hexyl and the like can be named.

In the definition of B, where "phenylene" is substituted, examples of substituents on the "phenylene" include, for example, halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, amino lower alkylcarbonyl and the like. The phenylene may be substituted with 1-3 substituents selected from those named above. Of those, particularly phenylene groups which are optionally substituted with one or two substituents selected from halogen, lower alkyl, lower alkoxy, cyano, halogeno-lower alkyl and lower alkylcarbonylamino are preferred.

"$C_1$-$C_{10}$ alkyl" said in the definition of $R^5$ signifies straight chain or branched chain alkyl groups containing 1-10 carbon atoms, examples of which including methyl, ethyl, n-propyl, isopropyl, n-butyl, isobutyl, sec-butyl, tert-butyl, n-pentyl, isopentyl, n-hexyl, n-heptyl, n-octyl, 3,3-dimethyl-n-hexyl, n-nonyl, n-decyl and the like. Of these, straight chain or branched chain $C_3$-$C_9$ alkyl, in particular straight chain $C_5$-$C_9$ alkyl, are preferred.

"Phenyl-lower alkyl (in which the phenyl moiety may be further substituted)" said in the definition of $R^5$ signifies lower alkyl which is substituted with either substituted or unsubstituted phenyl. As the substituents which may be present on the phenyl, those similar to the named substituents on above "phenylene" can be named.

Furthermore, "benzoyl-lower alkyl (in which the phenyl moiety in the benzoyl may be further substituted)" said in the definition of $R^5$ signifies lower alkyl which is substituted with benzoyl whose phenyl moiety may be substituted or unsubstituted. As the substituent(s) on the phenyl moiety of benzoyl group, those similar to the named substituents on above "phenylene" can be named.

As also the substituents on the phenyl in "substituted or unsubstituted phenyl" said in the definition of $R^5$, those similar to the named substituents on above "phenylene" can be named.

"Cycloalkyl-lower alkyl" said in the definition of $R^5$ signifies cycloalkyl-substituted lower alkyl. As preferred "cycloalkyl" herein, $C_4$-$C_8$ cycloalkyl, for example, cyclobutyl, cyclopentyl, cyclohexyl, cycloheptyl, cyclooctyl and the like can be named. Of these, particularly cyclopentyl and cyclohexyl are preferred. As the lower alkyl, for example, methyl, ethyl, n-propyl and n-butyl and the like are preferred. Thus, specific preferred examples of "cycloalkyl-lower alkyl" include cyclopentylmethyl, cyclopentylethyl, cyclopentyl-n-propyl, cyclopentyl-n-butyl, cyclohexylmethyl, cyclohexylethyl, cyclohexyl-n-propyl and cyclohexyl-n-butyl.

"Piperidinyl-lower alkyl" said in the definition of $R^5$ signifies piperidinyl-substituted lower alkyl, wherein the piperidinyl may bind to the lower alkyl at any of the positions 1-4, preferred binding position being 1 or 4.

"Amino" said in the definition of $R^5$ includes not only unsubstituted amino but also amino groups which are substituted with 1 or 2 alkyl groups and cyclic amino groups. As the alkyl herein, besides lower alkyl, for example, branched chain $C_7$-$C_{12}$ alkyl such as 1-(lower alkyl)ethyl, 1-(lower alkyl)-n-propyl, 2-(lower alkyl)-n-propyl, di(lower alkyl)methyl, 1,1-di(lower alkyl)ethyl, 1,1-di(lower alkyl)-n-propyl and the like can be named. Also as the cyclic amino, for example, 1-pyrrolidinyl, 1-piperidinyl, 1-azepinyl and the like can be named. Of those, particularly amino groups which are substituted with 1 or 2 branched chain $C_3$-$C_8$ alkyl groups and cyclic amino groups are preferred.

"Halogen" includes fluorine, chlorine, bromine and iodine.

A preferred group of compounds in the present invention are those of the formula (I) wherein both $R^1$ and $R^2$ stand for hydrogen.

Another preferred group of compounds in the present invention are those of the formula (I) wherein $R^3$ and $R^4$ stand for hydrogen or halogen, independently of each other, in particular, those compounds of the formula (I) wherein $R^3$ and $R^4$ stand for hydrogen or fluorine, independently of each other.

Still another preferred group of compounds in the present invention are those of the general formula (I) wherein B stands for $CH_2$ or $SO_2$.

Still a different group of compounds which are preferred in the present invention are those of the general formula (I) wherein $R^5$ stands for straight chain or branched chain $C_3$-$C_9$ alkyl, phenyl-lower alkyl (wherein the phenyl moiety may be further substituted), cycloalkyl-lower alkyl or substituted or unsubstituted phenyl. In particular, those compounds of the formula (I) wherein $R^5$ stands for substituted or unsubstituted phenyl are preferred.

As the straight chain or branched chain $C_3$-$C_9$ alkyl as defined as to $R^5$, in particular, n-butyl, n-pentyl, n-hexyl, n-heptyl, n-octyl or n-nonyl are preferred.

Also as the cycloalkyl-lower alkyl as defined as to $R^5$, in particular, cyclopentylmethyl, cyclopentylethyl, cyclopentyl-n-propyl, cyclopentyl-n-butyl, cyclohexylmethyl, cyclohexylethyl, cyclohexyl-n-propyl, or cyclohexyl-n-butyl are preferred.

Furthermore, as the substituted or unsubstituted phenyl as defined as to $R^5$, in particular, fluorophenyl or chlorophenyl are preferred.

As the typical examples of compounds of the formula (I) which are provided by the present invention, besides those described in later appearing working Examples, the following can be named:

2,5-difluoro-4-[4-(3-phenylpropyl)piperidino]phenyl-N-methyl-O-sulfamate, 2,5-difluoro-4-[4-(3-phenylpropyl)piperidino]phenyl-N-ethyl-O-sulfamate, 2,5-difluoro-4-[4-(3-phenylpropyl)piperidino]phenyl-N,N-di-methyl-O-sulfamate, 4-[4-(3-cyclohexylpropyl)piperazin-1-yl]-2,5-difluorophenyl-N-methyl-O-sulfamate, 4-[4-(3-cyclohexylpropyl)piperazin-1-yl]-2,5-difluorophenyl-N-ethyl-O-sulfamate, 4-[4-(3-cyclohexylpropyl)piperazin-1-yl]-2,5-difluorophenyl-N,N-dimethyl-O-sulfamate, 2-methyl-4-[4-(3-phenylpropyl)piperidino]phenyl-O-sulfamate, 2-ethyl-4-[4-(3-phenylpropyl)piperidino]phenyl-O-sulfamate, 2-isopropyl-4-[4-(3-phenylpropyl)piperidino]phenyl-O-sulfamate, 3-methyl-4-[4-(3-phenylpropyl)piperidino]phenyl-O-sulfamate, 2-cyano-4-[4-(3-phenylpropyl)piperidino]phenyl-O-sulfamate, 2-bromo-4-[4-(3-phenylpropyl)piperidino]phenyl-O-sulfamate, 2-iodo-4-[4-(3-phenylpropyl)piperidino]phenyl-O-sulfamate, 3-fluoro-4-[4-(3-phenylpropyl)piperidino]phenyl-O-sulfamate, 3-chloro-4-[4-(3-phenylpropyl)piperidino]phenyl-O-sulfamate, 2,5-dimethyl-4-[4-(3-phenylpropyl)piperidino]phenyl-O-sulfamate, 2-cyano-5-methyl-4-[4-(3-phenylpropyl)piperidino]phenyl-O-sulfamate, 5-cyano-2-methyl-4-[4-(3-phenylpropyl)piperidino]phenyl-O-sulfamate, 2-fluoro-5-methyl-4-[4-(3-phenylpropyl)piperidino]phenyl-O-sulfamate, 5-fluoro-2-methyl-4-[4-(3-phenylpropyl)piperidino]phenyl-O-sulfamate, 5-chloro-2-fluoro-4-[4-(3-phenylpropyl)piperidino]phenyl-O-sulfamate, 4-[4-(3-cyclohexylpropyl)piperazin-1-yl]-2-methylphenyl-O-sulfamate, 4-[4-(3-cyclohexylpropyl)piperazin-1-yl]-2-ethylphenyl-O-sulfamate, 4-[4-(3-cyclohexylpropyl)piperazin-1-yl]-2-isopropylphenyl-O-sulfamate, 4-[4-(3-cyclohexylpropyl)piperazin-1-yl]-3-methylphenyl-O-sulfamate, 2-cyano-4-[4-(3-cyclohexylpropyl)piperazin-1-yl]phenyl-O-sulfamate, 2-bromo-4-[4-(3-cyclohexylpropyl)piperazin-1-yl]phenyl-O-sulfamate, 4-[4-(3-cyclohexylpropyl)piperazin-1-yl]-2-iodophenyl-O-sulfamate, 4-[4-(3-cyclohexylpropyl)piperazin-1-yl]-3-fluorophenyl-O-sulfamate, 3-chloro-4-[4-(3-cyclohexylpropyl)piperazin-1-yl]phenyl-O-sulfamate, 4-[4-(3-cyclohexylpropyl)piperazin-1-yl]-2,5-dimethylphenyl-O-sulfamate, 2-cyano-4-[4-(3-cyclohexylpropyl)piperazin-1-yl]-5-methyl-phenyl-O-sulfamate,
5-cyano-4-[4-(3-cyclohexylpropyl)piperazin-1-yl]-2-methyl-phenyl-O-sulfamate,
4-[4-(3-cyclohexylpropyl)piperazin-1-yl]-2-fluoro-5-methyl-phenyl-O-sulfamate,
4-[4-(3-cyclohexylpropyl)piperazin-1-yl]-5-fluoro-2-methyl-phenyl-O-sulfamate,
5-chloro-4-[4-(3-cyclohexylpropyl)piperazin-1-yl]-2-fluorophenyl-O-sulfamate,
2,5-difluoro-4-[4-(2-phenylethyl)piperidino]phenyl-O-sulfamate,
4-{4-[3-(4-chlorophenyl)propyl]piperidino}-2,5-difluorophenyl-O-sulfamate,
2,5-difluoro-4-{4-[3-(4-methylphenyl)propyl]piperidino}phenyl-O-sulfamate,
4-{4-[3-(4-cyanophenyl)propyl]piperidino}-2,5-difluorophenyl-O-sulfamate,
2,5-difluoro-4-[4-(4-phenylbutyl)piperidino]phenyl-O-sulfamate,
4-[4-(2-cyclohexylethyl)piperidino]-2,5-difluorophenyl-O-sulfamate,
4-[4-(5-cyclohexylpentyl)piperidino]-2,5-difluorophenyl-O-sulfamate,
2,5-difluoro-4-[4-(4-methylhexyl)piperidino]phenyl-O-sulfamate,
4-(4-decylpiperidino)-2,5-difluorophenyl-O-sulfamate,
2,5-difluoro-4-[4-(2-oxo-2-phenylethyl)piperidino]phenyl-O-sulfamate,
4-[4-(diethylaminomethyl)piperidino]-2,5-difluorophenyl-O-sulfamate,
2,5-difluoro-4-[4-(3-methyl-1-oxobutyl)piperidino]phenyl-O-sulfamate,
2,5-difluoro-4-[4-(phenylcarbonyl)piperidino]phenyl-O-sulfamate,
2,5-difluoro-4-[4-(1-oxo-2-phenylethyl)piperidino]phenyl-O-sulfamate,
4-{4-[3-(4-chlorophenyl)-1-oxopropyl]piperidino}-2,5-difluorophenyl-O-sulfamate,
2,5-difluoro-4-{4-[3-(4-methylphenyl)-1-oxopropyl]piperidino}-phenyl-O-sulfamate,
4-{4-[3-(4-cyanophenyl)-1-oxopropyl]piperidino}-2,5-difluorophenyl-O-sulfamate,
2,5-difluoro-4-[4-(1-oxopentyl)piperidino]phenyl-O-sulfamate,
2,5-difluoro-4-[4-(1-oxodecyl)piperidino]phenyl-O-sulfamate,
4-[4-(3-cyclohexyl-1-oxopropyl)piperidino]-2,5-difluorophenyl-O-sulfamate,
4-(4-aminocarbonylpiperidino)-2,5-difluorophenyl-O-sulfamate,
(Z)-2,5-difluoro-4-[4-(1-nonen-1-yl)piperidino]phenyl-O-sulfamate,
(Z)-4-{4-[3-(4-chlorophenyl)-1-propen-1-yl]piperidino}-2,5-difluorophenyl-O-sulfamate,
(Z)-2,5-difluoro-4-{4-[3-(4-methylphenyl)-1-propen-1-yl]-piperidino}phenyl-O-sulfamate,
(Z)-4-{4-[3-(4-cyanophenyl)-1-propen-1-yl]piperidino}-2,5-difluorophenyl-O-sulfamate,
(Z)-2,5-difluoro-4-[4-(3-oxo-3-phenyl-1-propen-1-yl)piperidino]-phenyl-O-sulfamate,
(Z)-4-[4-(3-cyclohexyl-1-propen-1-yl)piperidino]-2,5-difluorophenyl-O-sulfamte,
(Z)-4-[4-(3-amino-1-propen-1-yl)piperidino]-2,5-difluorophenyl-O-sulfamte,
(Z)-2,5-difluoro-4-[4-(3-isopropylamino-1-propen-1-yl)-piperidino]phenyl-O-sulfamate,
4-[4-(4-chlorophenyl)piperidino]-2,5-difluorophenyl-O-sulfamate,
2,5-difluoro-4-[4-(4-methylphenyl)piperidino]phenyl-O-sulfamate,
4-[4-(4-cyanophenyl)piperidino]-2,5-difluorophenyl-O-sulfamate,
4-[4-(2,4-dichlorophenyl)piperidino]-2,5-difluorophenyl-O-sulfamate,
4-[4-(2-chloro-4-methylphenyl)piperidino]-2,5-difluorophenyl-O-sulfamate,
4-[4-(4-chloro-2-methylphenyl)piperidino]-2,5-difluorophenyl-O-sulfamate,
2,5-difluoro-4-[4-(4-hydroxyphenyl)piperidino]phenyl-O-sulfamate,
2,5-difluoro-4-[4-(4-methoxyphenyl)piperidino]phenyl-O-sulfamate,
4-[4-(4-aminophenyl)piperidino]-2,5-difluorophenyl-O-sulfamate,
2,5-difluoro-4-[4-(4-nitrophenyl)piperidino]phenyl-O-sulfamate,
4-[4-(4-chloromethylphenyl)piperidino]-2,5-difluorophenyl-O-sulfamate,
4-[4-(4-cyanomethylphenyl)piperidino]-2,5-difluorophenyl-O-sulfamate,
2,5-difluoro-4-[4-(4-methylaminophenyl)piperidino]phenyl-O-sulfamate,
4-[4-(4-diethylaminophenyl)piperidino]-2,5-difluorophenyl-O-sulfamate,
4-[4-(4-acetylaminophenyl)piperidino]-2,5-difluorophenyl-O-sulfamate,
4-[4-(4-acetylphenyl)piperidino]-2,5-difluorophenyl-O-sulfamate,
4-[4-(4-aminomethylcarbonylphenyl)piperidino]-2,5-difluorophenyl-O-sulfamate,
4-[4-(4-chlorophenyl)methylpiperazin-1-yl]-2,5-difluorophenyl-O-sulfamate,
2,5-difluoro-4-[4-(4-methylphenyl)methylpiperazin-1-yl]phenyl-O-sulfamate,
4-[4-(4-cyanophenyl)methylpiperazin-1-yl]-2,5-difluorophenyl-O-sulfamate,
4-[4-(4-amino-2-methylphenyl)methylpiperazin-1-yl]-2,5-di-fluorophenyl-O-sulfamate,
4-(4-cyclohexylmethylsulfonylpiperazin-1-yl)-2,5-difluorophenyl-O-sulfamate,
4-[4-(2-cyclohexylethyl)sulfonylpiperazin-1-yl]-2,5-difluorophenyl-O-sulfamate,
2,5-difluoro-4-(4-isopropylsulfonylpiperazin-1-yl)phenyl-O-sulfamate,
2,5-difluoro-4-(4-sulfamoylpiperazin-1-yl)phenyl-O-sulfamate,
2,5-difluoro-4-(4-isopropylsulfamoylpiperazin-1-yl)phenyl-O-sulfamate,
2,5-difluoro-4-[4-(2-phenylethyl)sulfonylpiperazin-1-yl]-phenyl-O-sulfamate,
4-[4-(3-cyclohexylpropanoyl)piperazin-1-yl]-2,5-difluorophenyl-O-sulfamate,
4-[4-(4-cyclohexylbutyryl)piperazin-1-yl]-2,5-difluorophenyl-O-sulfamate,
2,5-difluoro-4-[4-(4-phenylbutyryl)piperazin-1-yl]phenyl-O-sulfamate,
4-(4-chlorophenylpiperazin-1-yl)-2,5-difluorophenyl-O-sulfamate,
2,5-difluoro-4-(4-methylphenylpiperazin-1-yl)phenyl-O-sulfamate,
4-(4-cyanophenylpiperazin-1-yl)-2,5-difluorophenyl-O-sulfamate, and the like.

Those compounds of the formula (I) according to the present invention can form salts where necessary, depending on the kinds of substituents A and $R^5$. Examples of such salts include salts with inorganic acids such as hydrochloric acid, hydrobromic acid, sulfuric acid, nitric acid, phosphoric acid and the like; salts with organic acids such as acetic acid, oxalic acid, citric acid, lactic acid, tartaric acid, p-toluenesulfonic acid and the like; alkali metal salts such as sodium salt, potassium salt, lithium salt and the like; alkaline earth metal salts such as calcium salt, magnesium salt and the like; salts with organic base such as triethylamine, dicyclohexylamine, pyrrolidine, morpholine, pyridine and the like; and ammonium salt. Of those, pharmaceutically acceptable salts are preferred.

According to the present invention, compounds of the formula (I) can be prepared, for example, through reaction of cyclicamino-phenol derivatives of a formula,

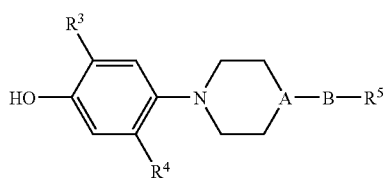

in which $R^3$, $R^4$, A, B and $R^5$ have the previously defined significations, with amidosulfonyl chloride of a formula,

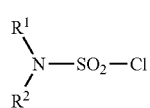

in which $R^1$ and $R^2$ have the previously defined significations.

The reaction can be conducted, generally in an inert solvent, for example, amides such as N,N-dimethylformamide, N,N-dimethylacetamide, N-methylpyrrolidone and the like; alkyl halides such as dichloromethane, dichloroethane and the like; or organic bases such as pyridine and the like, in the optional presence of alkalies such as sodium hydride, sodium methoxide, potassium butoxide, potassium hydroxide and the like; or organic bases such as triethylamine, 2,6-di-tert-butyl-4-methylpyridine and the like, at temperatures ranging from $-20°$ C. to the reflux temperature of the reaction mixture, preferable from $0°$ C. to room temperature.

The use rate of amidosulfonyl chloride of the formula (III) to the compound of the formula (II) is not subject to critical limitation, but in general terms it is convenient to use at least a mole, preferably 1.1-20 moles, inter alia, 2-10 moles, of amidosulfonyl chloride per mole of the compound of the formula (II). Also the alkali can be used within a range of from about 2-about 10 moles, per mole of the compound of the formula (II).

The compounds of the formula (I) wherein both $R^1$ and $R^2$ are hydrogen atoms can also be prepared through a reaction of a cyclicamino-phenol derivative of the formula (II) with chlorosulfonyl isocyanate and subsequent treatment with water.

The reaction of a cyclicamino-phenol derivative of the formula (II) with chlorosulfonyl isocyanate can be conducted generally in an inert solvent, for example, aromatic hydrocarbon such as toluene, xylene or the like; halogenated aromatic hydrocarbon such as chlorobenzene, dichlorobenzene or the like; or acetonitrile and the like, at temperature ranging from $50°$ C. to the reflux temperature of the reaction mixture, preferably from $80°$ C. to the reflux temperature of the reaction mixture.

The use rate of chlorosulfonyl isocyanate to the cyclicamino-phenol derivative of the formula (II) is not subject to any critical limitation, but in general terms it is adequate to use at least a mole, preferably 1.01-2 moles, of chlorosulfonyl isocyanate per mole of the compound of the formula (II).

The subsequent treatment with water can normally be easily conducted by adding water to the reaction mixture formed of the above reaction.

Thus a compound of the formula (I) which is intended by the present invention is obtained.

While most of the cyclic aminophenol derivatives of the formula (II) which are used as the starting material in the above resction are novel, they can be readily synthesized by methods similar to those for synthesizing known compounds, for example, by following the route as given in the following reaction scheme 1, 2 or 3. Where the phenolic hydroxyl groups in formed cyclic aminophenol derivatives are protected, the protective groups can be removed by a treatment with, for example, Louis acid such as boron tribromide, aluminium chloride or the like; acid such as conc. hydrochloric acid, hydrobromic acid and the like; or amine salt such as pyridine hydrochloride; or by hydrogenation. Concerning the particulars such as the reaction conditions, see Production Examples 9 and 13 given later, as to the reaction scheme 1; Production Examples 1, 3, 7 and 38 as to the reaction scheme 2; Production Examples 72-76, 79 and 80 as to the reaction scheme 3; and Production Examples 2, 10, 28, 30 and 94 as for deprotection of phenolic hydroxyl groups.

Binding of Cyclic Amine Compound to Phenolic Compound:

Reaction Scheme 1

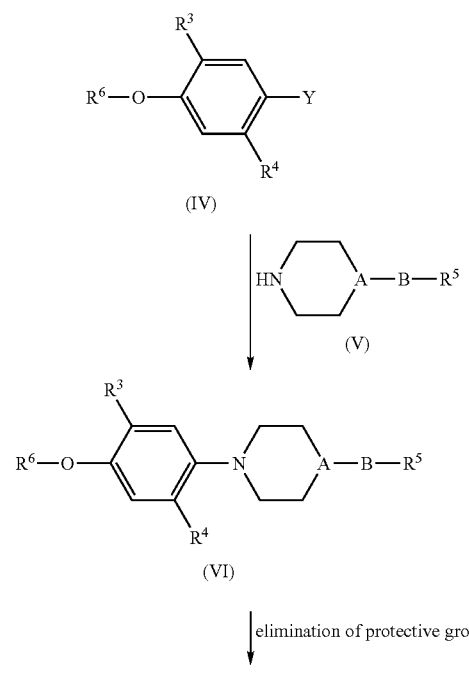

-continued
(II)

In the above formulae, $R^6$ stands for hydrogen or hydroxyl-protective group; Y stands for fluorine, chlorine or bromine; and $R^3$, $R^4$, $R^5$, A and B have the previously defined significations.

Binding of B—$R^5$ to piperazinyl-phenol Compound:

Reaction Scheme 2

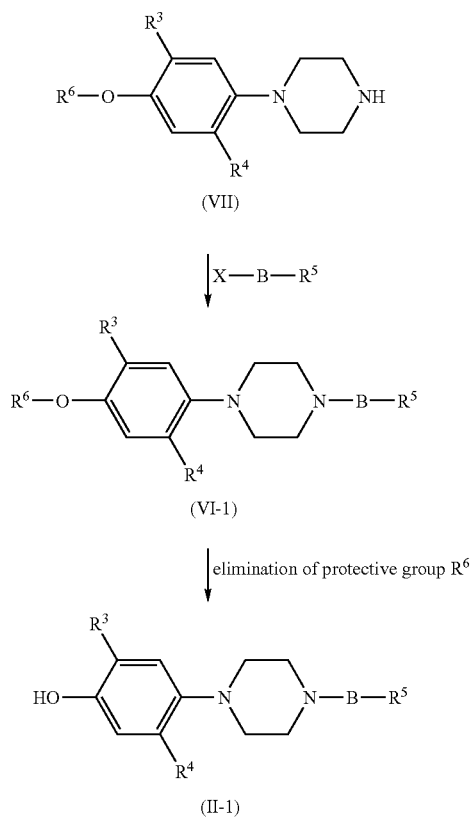

In the above formulae, X stands for chlorine, bromine or iodine; and $R^3$, $R^4$, $R^5$, $R^6$ and B have the previously defined significations.

Extension of Side Chain from cyclicamino-phenol Compound:

Reaction Scheme 3

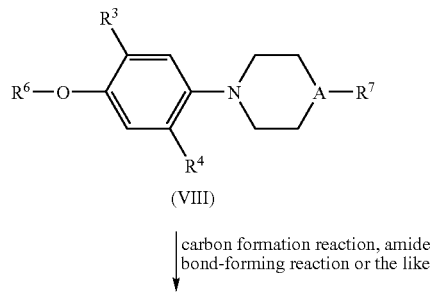

-continued

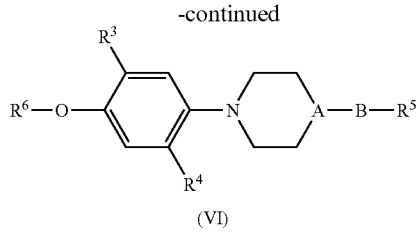

(VI)

↓ elimination of protective group $R^6$ (II)

In the above formulae, $R^7$ stands for a functional group such as formyl, carboxyl, hydroxymethyl or the like; and $R^3$, $R^4$, $R^5$, $R^6$, A and B have the previously defined significations.

In each of above-described reactions, when substituent(s) which are liable to participate in the reaction, for example, hydroxyl, amino, carboxyl and the like, are present in the reactant compounds, such substituents may be protected with protective groups where necessary. The protective groups can be eliminated after termination of the reaction.

Those compounds of the formula (I) which are prepared according to the above-described methods of the present invention can be isolated from the reaction mixtures and purified by the means known per se, for example, recrystallization, column chromatography, preparative thin layer chromatography and the like.

Those cyclicamino-phenyl sulfamate derivatives represented by the formula (I) which are provided by the present invention or salts thereof exhibit excellent steroid sulfatase inhibiting activity, and are useful as pharmaceuticals for therapy and treatment of diseases associated with steroids such as estrogen, androgen and the like, for example, breast cancer, corpus uteri cancer, ovarian cancer, endometrial hyperplasia, infertility, endometriosis, adenomyosis uteri, hysteromyoma, autoimmune disease, dementia, Alzheimer's disease, mastopathy, gynecomastia, benign prostate hyperplasia, men's infertility associated with oligospermia, androgen-dependent dermopathy and the like.

Steroid sulfatase inhibitory activity, estrogenic activity and absence of gene toxicity of compounds of the formula (I) can be demonstrated by the following experiments.

(1) Measurement of Steroid Sulfatase Inhibitory Activity (in vitro):

As the source of steroid sulfatase enzyme, microsomal fraction of MCF-7 human breast cancer cells was used.

To phosphate buffered saline (PBS), one of the test compounds, the microsomal fraction and 50 μL of 60 μM estrone-3-sulfate containing about 100 nCi of [6,7-$^3$H]estrone-3-sulfate (purchased from Perkin Elmer Life Sciences, Boston, Mass., USA; specific activity, 40-60 Ci/mmol) were added to make the total amount of the reaction system 150 μL, which was incubated at 37° C. for 30 minutes. After the incubation, 50 μL of PBS containing about 2 nCi of [4-$^{14}$C] estrone (purchased from Perkin Elmer Life Sciences, Boston, Mass., USA; specific activity 45-60 mCi/mmol) was added and stirred. Further 800 μL of toluene was added, and the whole system was thoroughly shaken for 30 seconds, followed by centrifugation at 2,000×g for 10 minutes to separate the acqueous phase from the organic phase. A part (400 μL) of the organic phase was taken and measured of its $^3$H and $^{14}$C contents with scintillation spectrometer.

The mass of hydrolyzed [6,7-$^3$H]estrone-3-sulfate was calculated from the count number of the obtained $^3$H (as corrected regarding the amount of the used organic phase and the recovered amount of [4-$^{14}$C]estrone) and the specific activity of the substrate ([6,7-$^3$H]estrone-3-sulfate) to determine the steroid sulfatase inhibitory rate of each test compound. The results were as shown in the following Table 1.

TABLE 1

| Example No. | Inhibitory rate (%) | |
|---|---|---|
| of compound | ($10^{-7}$ M) | ($10^{-6}$ M) |
| Example 22 | 85.0 | 97.3 |
| Example 24 | 31.1 | 88.8 |
| Example 37 | 93.6 | 98.9 |
| Example 43 | 87.0 | 98.5 |
| Example 45 | 88.6 | 98.5 |
| Example 48 | 95.9 | 100.0 |
| Example 52 | 99.3 | 100.0 |
| Example 55 | 97.5 | 100.0 |
| Example 56 | 98.4 | 99.9 |
| Example 59 | 95.4 | 99.0 |

(2) Measurement of Steroid Sulfatase Inhibitory Activity (in vivo):

To six/group of female SD rats which had undergone ovariectomy, the test compounds as each suspended in 0.5% polyoxyethylene (20) sorbitan monooleate (Tween 80) were orally administered once a day for seven days. On the next day of the last administration, the rats were sacrificed under ether anesthesia. The bodies were anatomized and their livers and uteri were extracted, which were washed with cooled PBS and stored below −70° C. The livers and uteri were separately minced with scissors and suspended in cooled PBS containing 250 mM sucrose. Each of the suspensions was homogenized with a homogenizer under cooling with ice, from which neclei and cell debris were eliminated by centrifugation at 2,000×g for 20 minutes (4° C.). Protein concentration of each of the supernatant was measured by Bradford's method (Anal. Biochem., 72, 248-254 (1976)).

To 2-200 μg of the supernatant protein mass and 50 μL of 60 μM estrone-3-sulfate containing about 100 nCi of [6,7-$^3$H] estrone-3-sulfate (purchased from Perkin Elmer Life Sciences, Boston, Mass., U.S.A.; specific activity, 40-60 Ci/mmol), PBS was added to make the total amount 150 μL, followed by incubation at 37° C. for 30 minutes. After the incubation, the amount of hydrolyzed [6,7-$^3$H]estrone-3-sulfate was calculated by a method similar to the in vitro measurement in (1) above. Also steroid sulfatase activity per mg of the protein was calculated, and from the amount of the hydrolyzed [6,7-$^3$H]estrone-3-sulfate and the calculated steroid sulfatase activity per mg of the protein, the tested compound's steroid sulfatase inhibitory rate was determined. The results were as shown in the following Table 2.

TABLE 2

| Example No. | Inhibitiory rate (0.5 mg/kg, p.o., %) | |
|---|---|---|
| of compound | Liver | Uterus |
| Example 22 | 99.85 | 99.98 |
| Example 24 | 98.30 | 97.87 |
| Example 37 | 99.85 | 99.95 |
| Example 43 | 99.90 | 99.98 |
| Example 45 | 99.09 | 99.32 |
| Example 56 | 99.37 | 99.81 |
| Example 59 | 100.00 | 100.00 |

(3) MCF-7 Cell Proliferation Measurement for Examining Estrogenic Activity:

Stimulation of MCF-7 cell proliferation induced by estrogenic activity of each test compound was measured.

MCF-7 cells were cultured in 10% fetal bovine serum (FBS)-containing RPMI 1640 medium which was free from Phenol Red, using a 75 cm$^2$ culture flask. Then the medium was changed to RPMI 1640 medium containing 10% of FBS from which emdogenous steroid had been eliminated by charcoal treatment but containing no Phenol Red. Renewing the medium every two days, the culture was continued for 4 days. By this step estrogen was removed from the MCF-7 cells.

The MCF-7 cells were seeded on 96-well plates, 2,000 cells per well, and cultured for 24 hours to immobilize the cells on the plate. After the cell immobilization, the medium in each well was changed to RPMI 1640 medium containing $10^{-6}$M test compound and 10% of charcoal-treated FBS but containing no Phenol Red, and the culture was continued for further 4 days, during which the medium was changed every day to one newly prepared before the use. Also control wells to which no test compound was added were provided.

After the end of the culture, the cell proliferation was measured by MTT (3-(4,5-dimethylthiazol-2-yl)-2,5-diphenyl-2H-tetrazolium bromide; Sigma-Aldrich Japan Co.) method. That is, an MTT solution as dissolved in PBS at a concentration of 5 mg/mL was added to the 96-well plate accommodating the cells, at a rate of 10 μL/well, followed by 2 hours' incubation at 37° C. After the end of the incubation, the medium was removed and the formazan which was taken into the cells and changed was dissolved with 100 μL of dimethylsulfoxide. Absorbance of the formazan was measured at wavelength 570 nm, using a microplate reader, subtracting the 630 nm background. The absorbance values of the test compound-treated well, as relative to that of the control well, were as shown in the following Table 3.

As shown by the Table 3, absorbance values of the wells to which the test compounds were added were invariably less than 150% of the absorbance of the control well, and it was confirmed that the test compounds were free of estrogenic activity.

TABLE 3

| Example No. of compound | Absorbance relative to that of the control well ($10^{-6}$ M, %) |
|---|---|
| Example 22 | 74.6 |
| Example 24 | 74.6 |
| Example 37 | 89.5 |
| Example 43 | 101.1 |
| Example 45 | 91.4 |
| Example 48 | 112.0 |
| Example 52 | 112.0 |
| Example 55 | 64.6 |
| Example 59 | 105.3 |

(4) Miniscreen Method for Examining Presence of Genetic Toxicity:

Reverse mutation-inducing activity of the test comounds on bacteira was examined by Miniscreen method (Environ. Mol. Mutagen., 35, 72-77). *Salmonella typhimurium* TA100 and TA98, and *Escherichia coli* WP2 uvrA strains were used for the test. The test was conducted by plate incorporation method as to both cases where metabolic activation was not conducted, or conducted. The dosages were set at six levels as 0, 10, 50, 100, 500 and 1,000 μg/well.

To the minimum glucose-agar medium formed on a 6-well plate, 0.02 mL of a test compound solution or a solvent, 0.1 mL of 0.1 M sodium-phosphate buffer (pH=7.4), 0.025 mL of the bacterial suspension and 0.5 mL of soft agar solution were added per well and mixed. Where metabolic activation was conducted, 0.1M sodium-phosphate buffer (pH=7.4) was replaced with 0.1 mL of Rat Liver S9mix. After the soft agar solution solidified, the bacterial strains were cultured at 37° C. for 48 hours. At the end of the culture the number of revertant colonies on the plate was visually counted using a colony counter. Reverse mutation inducing activity of each of the test compounds was judged to be positive where the number of the revertant colonies increased by twice or more than that in the solvent-added control well, and judged negative where the increase was equivalent to the control. The results of this test are shown in Table 4 appearing later, concurrently with the results of the following test (5).

(5) In vitro Micronucleus Cell Induction Test for Examining Genetic Toxicity:

Presence of micronucleited cell-inducing activity of the test compounds on cultured cells due to chromosome aberration was examined by in vitro micronucleus test (mutagenesis test, 3, 238-245) by Lab-Tek method. The test was conducted by continuous treatment method, using Chinese hamster lung fibroblast cells (CHL/IU cells). The test compound concentration was set at three levels: 50% proliferation inhibitory concentration ($IC_{50}$), and at the concentration levels attained by diluting it by common ratio one time and two times.

Intact CHL/IU cells were inoculated on a 4-well Lab-Tek chamber slide (Nalge Nunc) at a rate of $2.5 \times 10^4$ cells/well and cultured at 37° C. under a carbon dioxide gas concentration of 5% for 24 hours, using an Eagle's MEM medium (ICN) containing 10% calf serum (ICN) and 2 mM glutamine. After the end of the culture the medium was removed, and 1 mL of fresh medium containing a solvent or the test compound each at a concentration as would meet each of the above-designed concentration levels was added, followed by 24 hours' culture and then washing with 1 mL of physiological phosphate buffer which contained no $Ca^{2+}$ or $Mg^{2+}$. One (1) mL of 0.075 M aqueous potassium chloride solution was added and a 5 minutes' hypotonic treatment was conducted at room temperature. After termination of the hypotonic treatment, the cells were fixed with a fixative (methanol: acetic acid=99:1). The slide detached from the chamber was stained with an aqueous acrydine orange solution (40 µg/mL). One thousand (1000) cells per dose were observed with fluorescent microscope to count the cells having micronuclei. In the case wherein the micronucleited cells increased by a rate twice or more than that in the control well to which the solvent only had been added, the micronucleited cell induction activity was judged positive, and in the case wherein the increase rate was equivalent to that of the control, negative. The test results were as shown in the following Table 4, concurrently with the results of the test (4).

TABLE 4

| Example No. of compound | Miniscreen method | In vitro micronucleited cell induction test |
|---|---|---|
| Example 13 | negative | negative |
| Example 24 | " | " |
| Example 36 | " | " |
| Example 37 | " | " |
| Example 45 | " | " |
| Example 55 | " | " |

(6) Reverse Mutation Test Using Bacteria (Ames Test) for Examining Presence of Gentic Toxicity:

Reverse mutation-inducing activity on bacteria of the test compounds was examined by reverse mutation test using bacteria (Mutat. Res., 113, 173-215). The test was conducted by plate incorporation method using *Salmonella typhimurium* TA 100, TA 1535, TA 98 and TA 1537 strains and *Escherichia coli* WP 2 uvrA strains as to both cases of not conducting metabolic activation and conducting metabolic activation. The dosages were set at six levels as 10, 50, 100, 500, 1000 and 5,000 µg/well.

Into a sterilized test tube, 0.1 mL of a test compound or a solvent, 0.5 mL of sodium-phosphate buffer (pH=7.4), 0.1 mL of a bacterial suspension and 2 mL of soft agar solution were added and mixed. Where metabolic activation was conducted, 1M sodium-phosphate buffer (pH=7.4) was replaced with 0.5 mL of Rat Liver S9mix. The liquid mixture was superposed on the minimum glucose agar medium and after the superposed soft agar solution solidified, the system was cultured at 37° C. for 48 hours. At the end of the culture the number of colonies in which reverse mutation had been induced was visually counted with a colony counter. Reverse mutation inducing activity of each of the test compounds was judged to be positive where the number of the revertant colonies increased by twice or more than that in the solvent-added control well, and judged negative where the increase was equivalent to the control. The results of this test are shown in Table 5 appearing later, concurrently with the results of the following test (7).

(7) Chromosome Aberration Test Using Mammals' Cultured Cells, for Examining Genetic Toxicity:

Presence of clastogenic activity of the test compounds on cultured cells was examined by a chromosome aberration test using mammals' cultured cells (Mutat. Res., 48, 337-354). The test was conducted by short time treatment method and continuous treatment method, using Chinese hamster lung fibroblast cells (CHL/IU cells). The test compound concentration was set at three levels of: one at which the cell proliferation rate was less than 50% and at least 100 divided cells were observed, and two different levels below the first level, at different cell prolifiration rates.

Intact CHL/IU cells were inoculated on a cell culture dishes of each 60 mm in diameter, at a rate of $5 \times 10^3$ cells per dish, and cultured at 37° C. at a carbon dioxide gas concentration of 5% for 3 days, using Eagle's MEM medium containing 10 v/v % of newborn calf serum (Sanko Pure Chemical). After the end of the culture, the medium was removed and 5 mL of a fresh medium containing solvent or a test compound at the concentration levels designed as above was added to the dishes where the continuous treatment was intended. In the short time treatment in which no S9mix was added, 3 ML of the fresh medium similar to the above was added, and where S9mix was added, 3 mL of a fresh medium formed by adding 0.5 mL of S9mix to 2.5 mL of the fresh medium similar to the above was added to the respective dishes. In the short time treatment, the medium was removed after 6 hours' treatment, and the cultured product was washed with 2 mL of physiological phosphate buffer free of $Ca^{2+}$ and $Mg^{2+}$, followed by addition of 5 mL of the fresh medium containing none of the test compounds and subsequent 18 hours' culture. In the continuous treatment, the culture time was increased to 24 hours. In both the short time treatment and continuous treatment, 50 µL of 10 µg/mL colcemide solution was added at two hours preceding the end of the culture. After the end of the culture, the cells were detached by 0.25% trypsine solution and transferred into a centifugation tube. Each cell suspension was centrifuged at 1000 rpm for 5 minutes to be removed of the supernatant, and to the remainder 3 mL of 0.075 M aqueous potassium chloride solution was added, followed by 15 minutes' hypotonic treatment at 37° C. After removing the hypotonic solution by centrifugation, the cells were fixed with a fixative (methanol: acetic acid=3:1). The fixed cell suspension was added onto a slide glass dropwise and stained with 2% Giemsa's solution. One-hundred divided metaphase cells per dose were observed with optical microscope and the number of cells having structurally abnormal chromosomes and numerically abnormal chromosomes was counted. Clastogenic activity of test compound was judged negative where the ratio of the cells having chromosome aberration was 5% or less based on that in the solvent control; quasi-positive, where the ratio was 5-10%; and positive, where the ratio was 10% or more. The test results were as given in the following Table 5, shown concurrently with the results of test (6).

TABLE 5

|  | | Chromosome aberration test | |
| --- | --- | --- | --- |
| Example No. of compound | Ames test | Structural abnormality | Numerical abnormality |
| Example 24 | negative | negative | negative |
| Example 37 | " | " | " |
| Example 45 | " | " | " |

As above, those cyclicamino-phenyl sulfamate derivatives of the formula (I) and salts thereof of the present invention exhibit excellent steroid sulfatase inhibiting activity and are free of estrogenic activity and genetic toxicity. Hence they can be administered as steroid sulfatase inhibiting agent for prevention, therapy or treatment of diseases of mammals including humans, either orally or parenterally (e.g., intramuscular injection, intravenous injection, rectal administration, percutaneous administration or the like).

When the compounds of the present invention are used as medicines, they can be formulated into various preparation forms according to their intended utility, such as solid preparations (e.g., tablet, hard capsule, soft capsule, granule, powder, grain, pill, troche and the like); semi-solid preparations (e.g., suppository, ointment and the like); or liquid preparations (e.g., injection, emulsion, suspension, lotion, spray and the like). As non-toxic adjuvants useful for such preparations (e.g., excipient, binder, disintegrant, corrective, emulsifier and the like), for example, starch, gelatin, glucose, lactose, fructose, maltose, magnesium carbonate, talc, magnesium stearate, methylcellulose, carboxymethylcellulose or salts thereof, gum arabic, polyethylene glycol, p-hydroxybenzoic acid alkyl ester, syrup, ethanol, propylene glycol, petrolatum, Carbowax, glycerine, sesame oil, Panasate, sodium chloride, sodium sulfite, sodium phosphate, citric acid and the like can be named. Those medical preparations may also contain other therapeutically useful medicines.

The contents of compounds of the present invention in such medical preparations are variable depending on, e.g. the preparation form. Whereas, in general terms it is desirable for solid and semi-solid preparations to contain the compounds at a concentration within a range of 0.1-50% by weight, and for liquid preparations, at that within a range of 0.05-10% by weight.

Administration dosages of the compounds are variable over a broad range depending on the kind of object warm-blooded animals represented by humans, administration route, degree of seriousness of patient's symptoms, doctor's diagnosis and the like. Generally it can be 0.01-5 mg/kg, preferably 0.02-2 mg/kg, per day, but it is obviously permissible to administer less dosages than the above lower limit or more dosages than the above upper limit, depending on the degree of seriousness of individual patient's symptoms, doctor's diagnosis and the like. The dosages as above-described can be administered at one time or as divided into plural times per day.

EXAMPLES

Hereinafter the present invention is explained in further details, referring to working examples.

Example 1

4-(4-Isobutylpiperazin-1-yl)phenol (142 mg) was dissolved in N,N-dimethylacetamide (0.9 mL), and to which sulfamoyl chloride (210 mg) was added under cooling with ice, followed by 3 hours' stirring at room temperature. The reaction mixture was poured in saturated saline solution, rendered weakly alkaline with saturated aqueous sodium hydrogencarbonate solution, and the product was extracted with ethyl acetate. The organic layer was washed with saturated saline solution and dried over anhydrous magnesium sulfate. The crude product, which remained after distilling the solvent off, was purified on TLC (developer, chloroform: acetone=13:7) to provide 4-(4-isobutylpiperazin-1-yl)phenyl-O-sulfamate (100 mg).

$^1$H-NMR(DMSO-$d_6$, δ):0.87(6H, d, J=6.6 Hz), 1.72-1.86 (1H, m), 2.08(2H, d, J=7.3 Hz), 2.38-2.52(4H, m), 3.05-3.15 (4H, m), 6.93(2H, d, J=9.3 Hz), 7.10(2H, d, J=9.3 Hz), 7.78 (2H, s). MS(m/z):313($M^+$).

Example 2

Example 1 was repeated except that 4-(4-isobutylpiperazin-1-yl)-phenol was replaced with 4-(4-phenethylpiperazin-1-yl)phenol (28 mg) and the resulting crude product was purified on TLC (developer, chloroform: methanol=12:1), to provide 4-(4-phenethylpiperazin-1-yl)phenyl-O-sulfamate (27 mg).

$^1$H-NMR(DMSO-$d_6$, δ):2.38-2.53(2H, m), 2.58(4H, br s), 2.77(2H, t, J=7.7 Hz), 3.12(4H, br s), 6.95(2H, d, J=8.9 Hz), 7.10(2H, d, J=9.3 Hz), 7.12-7.31(5H, m), 7.78(2H, s). MS(m/z):361($M^+$).

Example 3

Example 1 was repeated except that 4-(4-isobutylpiperazin-1-yl)phenol was replaced with 4-(4-hydroxyphenyl)-1-isovaleryl-piperazine (124 mg) and the resulting crude product was purified on TLC (developer, chloroform: tetrahydrofuran=3:1), to provide 4-(4-isovalerylpiperazin-1-yl)phenyl-O-sulfamate (98 mg).

$^1$H-NMR(DMSO-$d_6$, δ):0.90(6H, d, J=6.6 Hz), 1.92-2.07 (1H, m), 2.21(2H, d, J=6.9 Hz), 3.00-3.16(4H, m), 3.50-3.63 (4H, m), 6.98(2H, d, J=9.2 Hz), 7.12(2H, d, J=9.3 Hz), 7.79 (2H, s). MS(m/z):341($M^+$).

Example 4

Example 1 was repeated except that 4-(4-isobutylpiperazin-1-yl)phenol was replaced with 1-benzoyl-4-(4-hydroxyphenyl)-piperazine (134 mg) and the resulting crude product was purified on TLC (developer, chloroform: methanol=14:1), to provide 4-(4-benzoyl-piperazin-1-yl)phenyl-O-sulfamate (146 mg).

$^1$H-NMR(DMSO-$d_6$, δ):3.15(4H, br s), 3.32-3.85(4H, m), 6.98(2H, d, J=9.3 Hz), 7.12(2H, d, J=8.9 Hz), 7.38-7.49(5H, m), 7.80(2H, s). MS(m/z):361($M^+$).

Example 5

Example 1 was repeated except that 4-(4-isobutylpiperazin-1-yl)phenol was replaced with 1-(4-chlorophenylacetyl)-4-(4-hydroxyphenyl)piperazine (200 mg) and the resulting crude product was purified on TLC (developer, chloroform: tetrahydrofuran=3:1), to provide 4-[4-(4-chlorophenylacetyl)piperazin-1-yl]phenyl-O-sulfamate (31 mg).

$^1$H-NMR(DMSO-$d_6$, δ):3.01-3.11(4H, m), 3.60(4H, br s), 3.77(2H, s), 6.95(2H, d, J=9.3 Hz), 7.11(2H, d, J=8.9 Hz), 7.23(2H, d, J=8.5 Hz), 7.33(2H, d, J=8.5 Hz), 7.79(2H, s). MS(m/z):411($M^+$+2), 409($M^+$).

Example 6

Example 1 was repeated except that 4-(4-isobutylpiperazin-1-yl)phenol was replaced with 1-benzylsulfonyl-4-(4-hydroxypheny)-piperazine (159 mg) and the resulting crude product was purified on TLC (developer, chloroform: methanol=14:1), to provide 4-(4-benzyl-sulfonylpiperazin-1-yl)phenyl-O-sulfamate (105 mg).

$^1$H-NMR(DMSO-$d_6$, δ):3.02-3.20(4H, m), 3.24(4H, br s), 4.47(2H, s), 6.98(2H, d, J=8.9 Hz), 7.12(2H, d, J=8.9 Hz), 7.28-7.52(5H, m), 7.80(2H, s). MS(m/z):411($M^+$).

Example 7

Example 1 was repeated except that 4-(4-isobutylpiperazin-1-yl)phenol was replaced with 2-methyl-4-(4-phenethylpiperazin-1-yl)phenol (132 mg) and the resulting crude product was purified on TLC (developer, chloroform: tetrahydrofuran=3:1), to provide 2-methyl-4-(4-phenethylpiperazin-1-yl)phenyl-O-sulfamate (38 mg).

$^1$H-NMR(DMSO-$d_6$, δ):2.52-2.63(6H, m), 2.79(2H, t, J=7.9 Hz), 3.10-3.17(4H, m), 6.78(1H, dd, J=3.1, 8.9 Hz), 6.83(1H, d, J=2.7 Hz), 7.11(1H, d, J=8.9 Hz), 7.13-7.30(5H, m), 7.81(2H, s). MS(m/z):375($M^+$).

Example 8

Example 1 was repeated except that 4-(4-isobutylpiperazin-1-yl)phenol was replaced with 3-methyl-4-(4-phenethylpiperazin-1-yl)phenol (413 mg) and the resulting crude product was purified on TLC (developer, chloroform: tetrahydrofuran=3:1), to provide 3-methyl-4-(4-phenethylpiperazin-1-yl)phenyl-O-sulfamate (280 mg).

$^1$H-NMR(DMSO-$d_6$, δ):2.53-2.69(6H, m), 2.78(2H, t, J=7.7 Hz), 2.80-2.90(4H, m), 7.02-7.10(3H, m), 7.14-7.32(5H, m), 7.83(2H, s). MS(m/z):375($M^+$).

Example 9

Example 1 was repeated except that 4-(4-isobutylpiperazin-1-yl)phenol was replaced with 5-hydroxy-2-(4-phenylpiperidino)-benzonitrile (40 mg) and the resulting crude product was purified on TLC (developer, chloroform: acetone=15:1), to provide 3-cyano-4-(4-phenylpiperidino)phenyl-O-sulfamate (23 mg).

$^1$H-NMR(CDCl$_3$, δ):1.92-2.10(4H, m), 2.61-2.76(1H, m), 2.88-3.07(2H, m), 3.71(2H, d, J=11.2 Hz), 4.99(2H, br s), 7.07(1H, d, J=8.9 Hz), 7.16-7.38(5H, m), 7.47(1H, dd, J=2.9, 9.1 Hz), 7.52(1H, d, J=2.7 Hz). MS(m/z):357($M^+$).

Example 10

Example 1 was repeated except that 4-(4-isobutylpiperazin-1-yl)phenol was replaced with 2-(4-benzylpiperidino)-5-hydroxybenzonitrile (37 mg) and the resulting crude product was purified on TLC (developer, chloroform: acetone=15:1), to provide 4-(4-benzylpiperidino)-3-cyanophenyl-O-sulfamate (33 mg).

$^1$H-NMR(CDCl$_3$, δ):1.45-1.62(2H, m), 1.62-1.75(1H, m), 1.79(2H, d, J=12.7 Hz), 2.61(2H, d, J=6.9 Hz), 2.78(2H, dd, J=10.0, 11.9 Hz), 3.58(2H, d, J=11.9 Hz), 4.98(2H, s), 6.99(1H, d, J=9.2 Hz), 7.10-7.36(5H, m), 7.41(1H, dd, J=2.7, 8.9 Hz), 7.49(1H, d, J=2.7 Hz). MS(m/z):371($M^+$).

Example 11

Example 1 was repeated except that 4-(4-isobutylpiperazin-1-yl)phenol was replaced with 5-hydroxy-2-[4-(3-phenylpropyl)-piperidino]benzonitrile (141 mg) and the resulting crude product was purified on TLC (developer, chloroform: acetone=18:1), to provide 3-cyano-4-[4-(3-phenylpropyl)piperidino]phenyl-O-sulfamate (136 mg).

$^1$H-NMR(CDCl$_3$, δ):1.31-1.51(5H, m), 1.62-1.73(2H, m), 1.82(2H, d, J=9.6 Hz), 2.62(2H, t, J=7.7 Hz), 2.79(2H, t, J=11.6 Hz), 3.58(2H, d, J=11.9 Hz), 4.97(2H, s), 6.99(1H, d, J=8.9 Hz), 7.13-7.31(5H, m), 7.42(1H, dd, J=2.9, 9.1 Hz), 7.48(1H, s). MS(m/z):399($M^+$).

Example 12

Example 1 was repeated except that 4-(4-isobutylpiperazin-1-yl)phenol was replaced with 5-hydroxy-2-(4-phenethylpiperazin-1-yl)benzonitrile (116 mg) and the resulting crude product was purified on TLC (developer, chloroform: methanol=10:1), to provide 3-cyano-4-(4-phenethylpiperazin-1-yl)phenyl-O-sulfamate (94 mg).

$^1$H-NMR(DMSO-$d_6$, δ):2.57-2.72(6H, m), 2.79(2H, t, J=7.9 Hz), 3.12-3.21(4H, m), 7.16-7.32(6H, m), 7.49(1H, dd, J=2.9, 9.1 Hz), 7.60(1H, d, J=2.7 Hz), 8.02(2H, s). MS(m/z):307($M^+$−79).

Example 13

Example 1 was repeated except that 4-(4-isobutylpiperazin-1-yl)phenol was replaced with 2-[4-(3-cyclohexylpropyl)piperazin-1-yl]-5-hydroxybenzonitrile (246 mg) and the resulting crude product was purified on TLC (developer, chloroform: methanol=10:1), to provide 3-cyano-4-[4-(3-cyclohexylpropyl)piperazin-1-yl]-phenyl-O-sulfamate (252 mg).

$^1$H-NMR(CDCl$_3$, δ):0.78-0.95(2H, m), 1.07-1.28(6H, m), 1.45-1.57(2H, m), 1.57-1.76(5H, m), 2.40(2H, t, J=7.9 Hz), 2.58-2.70(4H, m), 3.12-3.25(4H, m), 6.99(1H, d, J=8.9 Hz), 7.45(1H, dd, J=2.7, 8.9 Hz), 7.50(1H, d, J=2.7 Hz). MS(m/z):327($M^+$−79).

Example 14

Example 1 was repeated except that 4-(4-isobutylpiperazin-1-yl)phenol was replaced with 2-chloro-4-(4-phenethylpiperazin-1-yl)-phenol (87 mg) and the resulting crude product was purified on TLC (developer, chloroform: methanol=15:1), to provide 2-chloro-4-(4-phenethylpiperazin-1-yl)phenyl-O-sulfamate (47 mg).

$^1$H-NMR(DMSO-$d_6$, δ):2.47-2.64(6H, m), 2.75(2H, t, J=7.7 Hz), 3.14(4H, br s), 6.92(1H, dd, J=3.1, 9.3 Hz), 7.03 (1H, d, J=2.7 Hz), 7.17(1H, t, J=7.1 Hz), 7.20-7.31(5H, m), 8.00(2H, s). MS(m/z):397($M^+$+2), 395($M^+$).

Example 15

Example 1 was repeated except that 4-(4-isobutylpiperazin-1-yl)phenol was replaced with 2-chloro-4-[4-(3-cyclohexylpropyl)-piperazin-1-yl]phenol hydrochloride (200 mg) and the resulting crude product was purified on TLC (developer, chloroform: methanol=10:1), to provide 2-chloro-4-[4-(3-cyclohexylpropyl)piperazin-1-yl]phenyl-O-sulfamate (186 mg).

$^1$H-NMR(DMSO-d$_6$, δ):0.85(2H, m), 1.1-1.3(6H, m), 1.45 (2H, m), 1.67(5H, m), 2.27(2H, t, J=7.3 Hz), 2.46(4H, br t, J=4.6 Hz), 3.15(4H, br t, J=4.6 Hz), 6.93(1H, dd, J=3.1, 9.3 Hz), 7.03(1H, d, J=2.7 Hz), 7.28(1H, d, J=8.9 Hz), 8.03(2H, s). MS(m/z):415(M$^+$).

Example 16

Example 1 was repeated except that 4-(4-isobutylpiperazin-1-yl)phenol was replaced with 2-[4-(3-chloro-4-hydroxyphenyl)-piperazin-1-yl]-1-phenylethan-1-one (24 mg) and the resulting crude product was purified on TLC (developer, chloroform: methanol=15:1), to provide 2-chloro-4-[4-(2-phenyl-2-oxoethyl)piperazin-1-yl]phenyl-O-sulfamate (19 mg).

$^1$H-NMR(DMSO-d$_6$, δ):2.67(4H, br s), 3.18(4H, br s), 3.91(2H, br s), 6.92(1H, dd, J=2.9, 9.1 Hz), 7.04(1H, d, J=2.7 Hz), 7.28(1H, d, J=9.3 Hz), 7.51(2H, t, J=7.7 Hz), 7.62(1H, t, J=7.3 Hz), 7.93-8.09(4H, m). MS(m/z):411(M$^+$+2), 409(M$^+$).

Example 17

To a mixture of 2-chloro-4-(piperazin-1-yl)phenol hydrochloride (150 mg), N,N-dimethylacetamide (1.4 mL) and triethylamine (220 μL), 4-chlorobenzenesulfonyl chloride (122 mg) was added under cooling with ice, followed by 1.3 hours' stirring at the same temperature. Sulfamoyl chloride (243 mg) was added to the reaction mixture and the temperature was raised to room temperature, followed by 2.7 hours' stirring. The reaction mixture was poured into saturated saline solution to which ethyl acetate was added. The system was rendered weakly alkaline with saturated aqueous sodium hydrogencarbonate solution. The organic layer was separated, washed with saturated saline solution and dried over anhydrous magnesium sulfate. The crude product as remained after distilling the solvent off was purified on TLC (developer, chloroform: methanol=20:1) to provide 2-chloro-4-[4-(4-chlorophenylsulfonyl)piperazin-1-yl]phenyl-O-sulfamate (129 mg).

$^1$H-NMR(CDCl$_3$, δ):2.95-3.10(4H, m), 3.19-3.30(4H, m), 6.92(1H, dd, J=3.1, 9.2 Hz), 7.07(1H, d, J=2.7 Hz), 7.30(1H, d, J=8.9 Hz), 7.74(2H, d, J=8.5 Hz), 7.79(2H, d, J=8.9 Hz), 8.05(2H, s). MS(m/z):388(M$^+$–77), 386(M$^+$–79).

Example 18

Example 1 was repeated except that 4-(4-isobutylpiperazin-1-yl)phenol was replaced with 3-chloro-4-(4-phenethylpiperazin-1-yl)-phenol (26 mg) and the resulting crude product was purified on TLC (developer, chloroform: methanol=13:1), to provide 3-chloro-4-(4-phenethylpiperazin-1-yl)phenyl-O-sulfamate (27 mg).

$^1$H-NMR(DMSO-d$_6$, δ):2.53-2.70(6H, m), 2.78(2H, t, J=7.7 Hz), 2.98(4H, br s), 7.14-7.37(8H, m), 7.98(2H, s). MS(m/z):318(M$^+$–77), 316(M$^+$–79).

Example 19

Example 1 was repeated except that 4-(4-isobutylpiperazin-1-yl)phenol was replaced with 2-fluoro-4-(4-octylpiperazin-1-yl)-phenol (248 mg) and the resulting crude product was purified on TLC (developer, chloroform: methanol=13: 1), to provide 2-fluoro-4-(4-octylpiperazin-1-yl)phenyl-O-sulfamate (245 mg).

$^1$H-NMR(CDCl$_3$, δ): 0.87(3H, t, J=6.8 Hz), 1.13-1.40 (10H, m), 1.40-1.60(2H, m), 2.37(2H, t, J=7.7 Hz), 2.44-2.67 (4H, m), 3.03-3.25(4H, m), 6.53-6.70(2H, m), 7.16-7.30(1H, m). MS(m/z):387(M$^+$).

Example 20

Example 1 was repeated except that 4-(4-isobutylpiperazin-1-yl)phenol was replaced with 4-[4-(2-cyclohexylethyl) piperazin-1-yl]-2-fluorophenol (73 mg) and the resulting crude product was purified on TLC (developer, chloroform: methanol=12:1), to provide 4-[4-(2-cyclohexylethyl)piperazin-1-yl]-2-fluorophenyl-O-sulfamate (72 mg).

$^1$H-NMR(DMSO-d$_6$, δ):0.82-0.96(2H, m), 1.04-1.39(6H, m), 1.53-1.72(5H, m), 2.30(2H, br t, J=7.3 Hz), 2.44(4H, br s), 3.12(4H, br s), 6.72(1H, dd, J=2.3, 6.9 Hz), 6.87(1H, dd, J=2.9, 14.1 Hz), 7.19(1H, t, J=9.3 Hz), 7.98(2H, s). MS(m/z):385(M$^+$).

Example 21

Example 1 was repeated except that 4-(4-isobutylpiperazin-1-yl)phenol was replaced with 2-fluoro-4-(4-phenethylpiperazin-1-yl)-phenol (172 mg) and the resulting crude product was purified on TLC (developer, chloroform: methanol=15:1), to provide 2-fluoro-4-(4-phenethylpiperazin-1-yl)phenyl-O-sulfamate (154 mg).

$^1$H-NMR(DMSO-d$_6$, δ):2.57(6H, br s), 2.77(2H, br t, J=7.9 Hz), 3.16(4H, br s), 6.74(1H, dd, J=1.7, 9.1 Hz), 6.88 (1H, dd, J=2.9, 14.1 Hz), 7.12-7.31(6H, m), 7.98(2H, s). MS(m/z):379(M$^+$).

Example 22

Example 1 was repeated except that 4-(4-isobutylpiperazin-1-yl)phenol was replaced with 4-[2-(4-chlorophenyl) ethyl]-piperazin-1-yl]-2-fluorophenol (254 mg) and the resulting crude product was purified on TLC (developer, chloroform: tetrahydrofuran=4:1), to provide 4-[4-[2-(4-chlorophenyl)ethyl]piperazin-1-yl]-2-fluorophenyl-O-sulfamate (69 mg).

$^1$H-NMR(DMSO-d$_6$, δ):2.58(6H, br s), 2.79(2H, t, J=7.7 Hz), 3.17(4H, br s), 6.76(1H, dd, J=1.9, 9.3 Hz), 6.89(1H, dd, J=2.7, 13.9 Hz), 7.22(1H, t, J=9.3 Hz), 7.27(2H, d, J=6.6 Hz), 7.31(2H, d, J=6.6 Hz), 8.00(2H, s). MS(m/z):413(M$^+$).

Example 23

Example 1 was repeated except that 4-(4-isobutylpiperazin-1-yl)phenol was replaced with 4-[4-(3-cyclopentylpropyl)piperazin-1-yl]-2-fluorophenol hydrochloride (200 mg) and the resulting crude product was purified on TLC (developer, chloroform: methanol=10:1), to provide 4-[4-(3-cyclopentylpropyl)piperazin-1-yl]-2-fluorophenyl-O-sulfamate (175 mg).

$^1$H-NMR(DMSO-d$_6$, δ):1.06(2H, m), 1.29(2H, m), 1.40-1.62(6H, m), 1.73(3H, m), 2.29(2H, t, J=7.3 Hz), 2.46(4H, t, J=4.6 Hz), 3.15(4H, br t, J=4.6 Hz), 6.75(1H, dd, J=1.9, 9.2

Hz), 6.89(1H, dd, J=2.7, 13.9 Hz), 7.21(1H, t, J=9.2 Hz), 8.00(2H, s). MS(m/z):385(M⁺).

Example 24

Example 1 was repeated except that 4-(4-isobutylpiperazin-1-yl)phenol was replaced with 4-[4-(3-cyclohexylpropyl)piperazin-1-yl]-2-fluorphenol hydrochloride (1.17 g) to provide 4-[4-(3-cyclohexylpropyl)piperazin-1-yl]-2-fluorophenyl-O-sulfamate (1.13 g).

¹H-NMR(DMSO-d₆, δ):0.88(2H, m), 1.06-1.29(6H, m), 1.57-1.80(7H, m), 2.95-3.23(6H, m), 3.54(2H, br d, J=10.8 Hz), 3.85(2H, br d, J=12.7 Hz), 6.84(1H, dd, J=1.9, 8.9 Hz), 7.04(1H, dd, J=2.7, 13.5 Hz), 7.28(1H, t, J=9.2 Hz), 8.06(2H, s). MS(m/z):399(M⁺).

Example 25

Example 1 was repeated except that 4-(4-isobutylpiperazin-1-yl)phenol was replaced with 4-[4-(3-cyclohexylpropyl)piperazin-1-yl]-2-fluorophenol (197 mg) to provide 4-[4-(3-cyclohexylpropyl)-piperazin-1-yl]-2-fluorophenyl-O-sulfamate (228 mg).

Example 26

Example 1 was repeated except that 4-(4-isobutylpiperazin-1-yl)phenol was replaced with 2-fluoro-4-[4-(3-phenylpropyl)-piperazin-1-yl]phenol (217 mg) and the resulting crude product was purified on TLC (developer, chloroform: acetone=3:1), to provide 2-fluoro-4-[4-(3-phenylpropyl)piperazin-1-yl]phenyl-O-sulfamate (83 mg).

¹H-NMR(DMSO-d₆, δ):1.72-1.83(2H, m), 2.27-2.39(2H, br), 2.48(4H, br s), 2.62(2H, t, J=7.5 Hz), 3.17(4H, s), 6.72-6.78(1H, m), 6.86-6.93 (1H, m), 7.13-7.32(6H, m), 8.00(2H, s). MS(m/z):393(M⁺).

Example 27

Example 1 was repeated except that 4-(4-isobutylpiperazin-1-yl)phenol was replaced with 1-(4-tert-butylphenyl)-4-[4-(3-fluoro-4-hydroxyphenyl)piperazin-1-yl]-1-butanone hydrochloride (190 mg) and the resulting crude product was hot-suspended in ethyl acetate, to provide 4-[[4-(4-tert-butylphenyl)-4-oxobutyl]piperazin-1-yl]-2-fluorophenyl-O-sulfamate (119 mg).

¹H-NMR(DMSO-d₆, δ):1.31(9H, s), 1.86(2H, m), 2.95-3.20(6H, m), 6.75(1H, br d, J=7.3 Hz), 6.89(1H, br d, J=13.9 Hz), 7.22(1H, t, J=9.2 Hz), 7.54, 7.90(4H, AB, J=8.5 Hz), 8.02(2H, s). MS(m/z):398(M⁺-H₂NSO₂+1).

Example 28

Example 1 was repeated except that 4-(4-isobutylpiperazin-1-yl)phenol was replaced with 4-(3-fluoro-4-hydroxyphenyl)-1-valerylpiperazine (56 mg) and the resulting crude product was purified on TLC (developer, chloroform: methanol=15:1), to provide 2-fluoro-4-(4-valerylpiperazin-1-yl) phenyl-O-sulfamate (15 mg).

¹H-NMR(CDCl₃, δ):0.86(3H, t, J=7.3 Hz), 1.21-1.38(2H, m), 1.40-1.53(2H, m), 2.32(2H, t, J=7.5 Hz), 3.13(4H, br d, J=20.8 Hz), 3.48-3.60(4H, m), 6.77(1H, dd, J=2.7, 9.6 Hz), 6.91(1H, d, J=13.9 Hz), 7.22(1H, t, J=9.1 Hz), 8.00(2H, s). MS(m/z):359(M⁺).

Example 29

Example 17 was repeated except that 2-chloro-4-(piperazin-1-yl)phenol hydrochloride and 4-chlorobenzenesulfonyl chloride were replaced with 2-fluoro-4-(piperazin-1-yl) phenol hydrochloride (150 mg) and 4-chlorobenzoyl chloride (86 μL), respectively, and the resulting crude product was purified on TLC (developer, chloroform: methanol=18:1). Thus 2-fluoro-4-[4-(4-chlorobenzoyl)piperazin-1-yl]phenyl-O-sulfamate (119 mg) was obtained.

¹H-NMR(DMSO-d₆, δ):3.21(4H, br s), 3.35-3.83(4H, m), 6.79(1H, dd, J=1.9, 8.9 Hz), 6.95(1H, d, J=13.7 Hz), 7.24(1H, t, J=9.1 Hz), 7.48(2H, d, J=8.5 Hz), 7.53(2H, d, J=8.9 Hz), 8.05(2H, s). MS(m/z):413(M⁺).

Example 30

Example 1 was repeated except that 4-(4-isobutylpiperazin-1-yl)phenol was replaced with N,N-diethyl-4-(3-fluoro-4-hydroxyphenyl)-1-piperazinecarboxamide (156 mg) and the resulting crude product was purified on TLC (developer, chloroform: methanol=13:1), to provide 4-[4-(N,N-diethylcarbamoyl)-piperazin-1-yl]-2-fluorophenyl-O-sulfamate (24 mg).

¹H-NMR(CDCl₃, δ):1.12(6H, t, J=7.7 Hz), 3.10-3.18(4H, m), 3.23(4H, q, J=6.9 Hz), 3.28-3.40(4H, m), 5.02(2H, s), 6.60-6.73(2H, m), 7.23-7.33(1H, m). MS(m/z):374(M⁺).

Example 31

Example 17 was repeated except that 2-chloro-4-(piperazin-1-yl)phenol hydrochloride and 4-chlorobenzenesulfonyl chloride were replaced with 2-fluoro-4-(piperazin-1-yl) phenol hydrochloride (200 mg) and pentylsulfonyl chloride (181 mg), to provide 2-fluoro-4-(4-pentylsulfonylpiperazin-1-yl)phenyl-O-sulfamate (169 mg).

¹H-NMR(DMSO-d₆, δ):0.87(3H, t, J=7.3 Hz), 1.26-1.41 (3H, m), 1.64-1.90(3H, m), 3.07(1H, m), 3.60(1H, m), 6.81 (1H, td, J=1.4, 8.9 Hz), 6.97(1H, dd, J=2.7, 13.9 Hz), 7.25 (1H, t, J=9.2 Hz), 8.03(2H, s). MS(m/z):409(M⁺).

Example 32

Example 17 was repeated except that 2-chloro-4-(piperazin-1-yl)phenol hydrochloride was replaced with 2-fluoro-4-(piperazin-1-yl)phenol hydrochloride (150 mg). The resulting crude product was purified on TLC (developer, chloroform: methanol=18:1), to provide 4-[4-(4-chlorophenylsulfonyl)piperazin-1-yl]-2-fluorophenyl-O-sulfamate (115 mg).

¹H-NMR(CDCl₃, δ):3.10-3.19(4H, m), 3.19-3.32(4H, m), 4.92(2H, s), 6.55-6.68(2H, m), 7.20-7.32(1H, m), 7.53(2H, d, J=8.5 Hz), 7.71(2H, d, J=8.5 Hz). MS(m/z):372(M⁺-77), 370(M⁺-79).

Example 33

Example 17 was repeated except that the 2-chloro-4-(piperazin-1-yl)phenol hydrochloride and 4-chlorobenzenesulfonyl chloride were replaced with 2-fluoro-4-(piperazin-1-yl) phenol hydrochloride (190 mg) and 4-chlorobenzylsulfonyl chloride (153 mg), to provide 4-[4-[(4-chlorophenyl)methylsulfonyl]piperazin-1-yl]-2-fluorophenyl-O-sulfamate (196 mg).

¹H-NMR(DMSO-d₆, δ):3.18-3.27(8H, m), 4.50(2H, s), 6.79(1H, dd, J=1.5, 8.9 Hz), 6.96(1H, dd, J=1.3, 6.7 Hz), 7.24(1H, t, J=8.9 Hz), 7.46(4H, s), 8.02(2H, s). MS(m/z):463 (M⁺).

Example 34

Example 1 was repeated except that 4-(4-isobutylpiperazin-1-yl)phenol was replaced with 3-fluoro-4-(4-phenethylpiperazin-1-yl)phenol (175 mg) and the resulting crude product was purified on TLC (developer, chloroform: methanol=14:1), to provide 3-fluoro-4-(4-phenethylpiperazin-1-yl)phenyl-O-sulfamate (138 mg).

$^1$H-NMR(DMSO-$d_6$, δ):2.55-2.70(6H, m), 2.78(2H, t, J=7.7 Hz), 3.02(4H, br s), 7.02-7.15(3H, m), 7.15-7.36(5H, m), 7.95(2H, s). MS(m/z):379(M$^+$).

Example 35

Example 1 was repeated except that 4-(4-isobutyl-piperazin-1-yl)phenol was replaced with 4-(4-benzylpiperidino)-2,5-difluorophenol (138 mg), to provide 4-(4-benzylpiperidino)-2,5-difluorophenyl-O-sulfamate (173 mg).

$^1$H-NMR(DMSO-$d_6$, δ):1.34(2H, m), 1.55-1.75(3H, m), 2.5-2.7(4H, m), 6.95-7.25(7H, m), 8.17(2H, s). MS(m/z):382 (M$^+$).

Example 36

Example 1 was repeated except that 4-(4-isobutylpiperazin-1-yl)phenol was replaced with 4-[4-(3-cyclohexylpropyl)piperidino]-2,5-difluorophenol (599 mg) and the resulting crude product was purified on TLC (developer, hexane: ethyl acetate=3:1), to provide 4-[4-(3-cyclohexylpropyl)piperidino]-2,5-difluorophenyl-O-sulfamate (223 mg).

$^1$H-NMR(CDCl$_3$, δ):0.8-0.9(2H, m), 1.1-1.4(14H, m), 1.6-1.8(6H, m), 2.62(2H, t, J=12 Hz), 3.41(2H, d, J=12 Hz), 4.95(2H, br s), 6.73(1H, dd, J=8, 12 Hz), 7.10(1H, dd, J=7, 12 Hz). MS(m/z):416(M$^+$), 336.

Example 37

Example 1 was repeated except that 4-(4-isobutylpiperazin-1-yl)phenol was replaced with 2,5-difluoro-4-[4-(3-phenylpropyl)-piperidino]phenol (66 mg) and the resulting crude product was purified on TLC (developer, chloroform: acetone=19:1), to provide 2,5-difluoro-4-[4-(3-phenylpropyl)piperidino]phenyl-O-sulfamate (70 mg).

$^1$H-NMR(CDCl$_3$, δ):1.29-1.47(5H, m), 1.61-1.72(2H, m), 1.78(2H, d, J=9.6 Hz), 2.56-2.70(4H, m), 3.42(2H, d, J=11.9 Hz), 4.97(2H, s), 6.72(1H, dd, J=7.7, 12.3 Hz), 7.10(1H, dd, J=7.3, 11.9 Hz), 7.13-7.33(5H, m). MS(m/z):410(M$^+$).

Example 38

Example 1 was repeated except that 4-(4-isobutylpiperazin-1-yl)phenol was replaced with (Z)-2,5-difluoro-4-[4-(3-phenyl-1-propen-1-yl)piperidino]phenol (48 mg) and the resulting crude product was purified on TLC (developer, hexane: ethyl acetate=3:1), to provide (Z)-2,5-difluoro-4-[4-(3-phenyl-1-propen-1-yl)-piperidino]-phenyl-O-sulfamate (18 mg).

$^1$H-NMR(CDCl$_3$, δ):1.55-1.68(2H, m), 1.71-1.80(2H, m), 2.5-2.6(1H, m), 2.67-2.76(2H, m), 3.40-3.47(4H, m), 4.94 (2H, br s), 5.38-5.44(1H, m), 5.5-5.6(1H, m), 6.74(1H, dd, J=8, 12 Hz), 7.12(1H, dd, J=7, 12 Hz), 7.16-7.22(3H, m), 7.26-7.32(2H, m). MS(m/z):408(M$^+$), 329, 289.

Example 39

Example 1 was repeated except that 4-(4-isobutylpiperazin-1-yl)phenol was replaced with 1-(2,5-difluoro-4-hydroxyphenyl)-N-(1-ethylpropyl)-4-piperidinecarboxamide (92 mg) and the resulting crude product was purified on TLC (developer, chloroform: methanol=12:1), to provide 4-[4-[N-(1-ethylpropyl)carbamoyl]piperidino]-2,5-difluorophenyl-O-sulfamate (63 mg).

$^1$H-NMR(DMSO-$d_6$, δ):0.80(6H, t, J=7.5 Hz), 1.22-1.36 (2H, m), 1.36-1.50(2H, m), 1.65-1.79(4H, m), 2.21-2.32(1H, m), 2.62-2.73(2H, m), 3.38(2H, d, J=12.0 Hz), 3.47-3.59(1H, m), 7.06(1H, dd, J=8.2, 12.0 Hz), 7.21(1H, dd, J=7.3, 12.7 Hz), 7.42(1H, d, J=8.9 Hz), 8.17(2H, s). MS(m/z):405(M$^+$).

Example 40

Example 1 was repeated except that 4-(4-isobutylpiperazin-1-yl)phenol was replaced with 1-[1-(2,5-difluoro-4-hydroxyphenyl)-4-piperidylcarbonyl]piperidine (172 mg) and the resulting crude product was purified on TLC (developer, chloroform: methanol=14:1), to provide 2,5-difluoro-4-[4-(piperidinocarbonyl)piperidino]phenyl-O-sulfamate (125 mg).

$^1$H-NMR(DMSO-$d_6$, δ):1.37-1.80(10H, m), 2.70-2.83 (3H, m), 3.33-3.52(6H, m), 7.02(1H, dd, J=8.3, 12.1 Hz), 7.22(1H, dd, J=7.3, 12.7 Hz), 8.18(2H, s). MS(m/z):403(M$^+$).

Example 41

Example 1 was repeated except that 4-(4-isobutylpiperazin-1-yl)phenol was replaced with 4-(4-decylpiperazin-1-yl)-2,5-difluorophenol (64 mg) and the resulting crude product was purified on TLC (developer, chloroform: methanol=15:1), to provide 4-(4-decylpiperazin-1-yl)-2,5-difluorophenyl-O-sulfamate (61 mg).

$^1$H-NMR(CDCl$_3$, δ):0.89(3H, t, J=6.9 Hz), 1.20-1.39 (14H, m), 1.43-1.60(2H, m), 2.40(2H, t, J=7.9 Hz), 2.52-2.69 (4H, m), 3.00-3.17(4H, m), 6.72(1H, dd, J=7.7, 12.0 Hz), 7.13(1H, dd, J=7.3, 12.0 Hz). MS(m/z):433(M$^+$).

Example 42

Example 1 was repeated except that 4-(4-isobutylpiperazin-1-yl)phenol was replaced with 4-[4-(2-cyclohexylethyl)piperazin-1-yl]-2,5-difluorophenol (85 mg) and the resulting crude product was purified on TLC (developer, chloroform: methanol=12:1), to provide 4-[4-(2-cyclohexylethyl)piperazin-1-yl]-2,5-difluorophenyl-O-sulfamate (86 mg).

$^1$H-NMR(DMSO-$d_6$, δ):0.82-0.96(2H, m), 1.05-1.40(6H, m), 1.53-1.74(5H, m), 2.33(2H, t, J=7.5 Hz), 2.38-2.53(4H, m), 2.93-3.07 (4H, m), 7.05(1H, dd, J=8.3, 12.2 Hz), 7.22 (1H, dd, J=7.3, 12.7 Hz), 8.18(2H, s). MS(m/z):403(M$^+$).

Example 43

Example 1 was repeated except that 4-(4-isobutylpiperazin-1-yl)phenol was replaced with 2,5-difluoro-4-(4-phenethylpiperazin-1-yl)phenol (467 mg) and the resulting crude product was purified on TLC (developer, chloroform: tetrahydrofuran=4:1), to provide 2,5-difluoro-4-(4-phenethylpiperazin-1-yl)phenyl-O-sulfamate (406 mg).

$^1$H-NMR(DMSO-$d_6$, δ):2.53-2.67(6H, m), 2.78(2H, t, J=8.3 Hz), 3.00-3.10(4H, m), 7.07(1H, dd, J=8.1, 12.3 Hz), 7.13-7.32(6H, m), 8.18(2H, br s). MS(m/z):318(M$^+$–79).

Example 44

Example 1 was repeated except that 4-(4-isobutylpiperazin-1-yl)phenol was replaced with 4-[4-(3-cyclopentylpropyl)piperazin-1-yl]-2,5-difluorophenol (80 mg) and the resulting crude product was purified on TLC (developer, chloroform: methanol=10:1), to provide 4-[4-(3-cyclopentylpropyl)piperazin-1-yl]-2,5-difluorophenyl-O-sulfamate (86 mg).

$^1$H-NMR(DMSO-d$_6$, δ):0.97-1.12(2H, m), 1.22-1.35(2H, m), 1.38-1.65(6H, m), 1.67-1.80(3H, m), 2.30(2H, t, J=7.3 Hz), 2.40-2.58(4H, m), 2.96-3.07(4H, m), 7.06(1H, dd, J=8.3, 12.1 Hz), 7.22(1H, dd, J=7.3, 12.3 Hz), 8.19(2H, s). MS(m/z):403(M$^+$).

Example 45

Example 1 was repeated except that 4-(4-isobutylpiperazin-1-yl)phenol was replaced with 4-[4-(3-cyclohexylpropyl)piperazin-1-yl]-2,5-difluorophenol (190 mg) and the resulting crude product was purified on TLC (developer, ethyl acetate: hexane=2:1), to provide 4-[4-(3-cyclohexylpropyl)piperazin-1-yl]-2,5-difluorophenyl-O-sulfamate (167 mg).

$^1$H-NMR(DMSO-d$_6$, δ):0.8-0.9(2H, m), 1.0-1.3(6H, m), 1.37-1.48(2H, m), 1.56-1.71(5H, m), 2.28(2H, br t, J=7 Hz), 2.4-2.5(4H, m), 3.01(4H, br t, J=4 Hz), 7.03(1H, dd, J=8, 12 Hz), 7.21(1H, dd, J=7, 13 Hz), 8.16(2H, s). MS(m/z):417(M$^+$), 338, 306, 227.

Example 46

Example 1 was repeated except that 4-(4-isobutylpiperazin-1-yl)phenol was replaced with 4-[4-(4-cyclohexylbutyl)piperazin-1-yl]-2,5-difluorophenol (122 mg) and the resulting crude product was purified on TLC (developer, chloroform: methanol=11:1), to provide 4-[4-(4-cyclohexylbutyl)piperazin-1-yl]-2,5-difluorophenyl-O-sulfamate (95 mg).

$^1$H-NMR(DMSO-d$_6$, δ):0.78-0.92(2H, m), 1.06-1.36(8H, m), 1.37-1.50(2H, m), 1.55-1.73(5H, m), 2.32(2H, t, J=7.2 Hz), 2.40-2.58(4H, m), 2.98-3.10(4H, m), 7.05(1H, dd, J=8.3, 12.1 Hz), 7.23(1H, dd, J=7.3, 12.7 Hz), 8.20(2H, s). MS(m/z):431(M$^+$).

Example 47

Example 1 was repeated except that 4-(4-isobutylpiperazin-1-yl)phenol was replaced with 3-[4-(2,5-difluoro-4-hydroxyphenyl)-piperazin-1-yl]-1-phenylpropan-1-one (334 mg) and the resulting crude product was purified on TLC (developer, ethyl acetate: hexane=2:1), to provide 2,5-difluoro-4-[4-(3-oxo-3-phenylpropyl)piperazin-1-yl]phenyl-O-sulfamate (96 mg).

$^1$H-NMR(DMSO-d$_6$, δ):2.5-2.6(4H, m), 2.74(2H, br t, J=7 Hz), 2.98-3.06(4H, m), 7.04(1H, dd, J=7, 12 Hz), 7.22(1H, dd, J=7, 12 Hz), 7.49-7.55(2H, m), 7.60-7.65(1H, m), 7.96-8.01(2H, m), 8.16(2H, br s). MS(m/z):346(M$^+$-SO$_2$NH), 331.

Example 48

Example 1 was repeated except that 4-(4-isobutylpiperazin-1-yl)phenol was replaced with 1-(4-tert-butylphenyl)-4-[4-(2,5-difluoro-4-hydroxyphenyl)piperazin-1-yl]-1-butanone (213 mg) and the resulting crude product was purified on TLC (developer, ethyl acetate), to provide 4-[4-[4-(4-tert-butylphenyl)-4-oxobutyl]piperazin-1-yl]-2,5-difluorophenyl-O-sulfamate (115 mg).

$^1$H-NMR(CDCl$_3$, δ):1.34(9H, s), 1.9-2.0(2H, m), 2.48(2H, t, J=7 Hz), 2.5-2.7(4H, m), 3.0-3.1(6H, m), 6.70(1H, dd, J=8, 12 Hz), 7.13(1H, dd, J=7, 12 Hz), 7.48(2H, d, J=8 Hz), 7.92(2H, d, J=8 Hz). MS(m/z):416(M$^+$-SO$_2$NH), 401, 240.

Example 49

Example 1 was repeated except that 4-(4-isobutylpiperazin-1-yl)phenol was replaced with 1-decanoyl-4-(2,5-difluoro-4-hydroxyphenyl)piperazine (265 mg) and the resulting crude product was purified on TLC (developer, chloroform: methanol=17:1), to provide 4-(4-decanoylpiperazin-1-yl)-2,5-difluorophenyl-O-sulfamate (247 mg).

$^1$H-NMR(DMSO-d$_6$, δ):0.85(3H, t, J=6.9 Hz), 1.25(12H, br s), 1.42-1.55(2H, m), 2.32(2H, t, J=7.5 Hz), 2.90-3.06(4H, m), 3.50-3.65(4H, m), 7.07(1H, dd, J=8.3, 12.2 Hz), 7.25(1H, dd, J=7.3, 12.7 Hz), 8.20(2H, s). MS(m/z) :447(M$^+$).

Example 50

Example 1 was repeated except that 4-(4-isobutylpiperazin-1-yl)phenol was replaced with 1-(4-tert-butylbenzoyl)-4-(2,5-difluoro-4-hydroxyphenyl)piperazine (200 mg) and the resulting crude product was purified on TLC (developer, chloroform: methanol=18:1), to provide 4-[4-(4-tert-butylbenzoyl)piperazin-1-yl]-2,5-difluorophenyl-O-sulfamate (199 mg).

$^1$H-NMR(CDCl$_3$, δ):1.31(9H, s), 3.07(4H, br s), 3.52-4.03 (4H, m), 5.17(2H, s), 6.72(1H, dd, J=7.9, 11.8 Hz), 7.13(1H, dd, J=7.3, 11.9 Hz), 7.37(2H, d, J=6.4 Hz), 7.42(2H, d, J=6.4 Hz). MS(m/z):453(M$^+$).

Example 51

Example 1 was repeated except that 4-(4-isobutylpiperazin-1-yl)phenol was replaced with 4-(2,5-difluoro-4-hydroxyphenyl)-1-(3-phenylpropanoyl)piperazine (243 mg) and the resulting crude product was purified on TLC (developer, chloroform: methanol=15:1), to provide 2,5-difluoro-4-[4-(3-phenylpropanoyl)piperazin-1-yl]-phenyl-O-sulfamate (228 mg).

$^1$H-NMR(DMSO-d$_6$, δ):2.63(2H, t, J=7.7 Hz), 2.81(2H, t, J=7.5 Hz), 2.88-2.99(4H, m), 3.50-3.64(4H, m), 7.04(1H, dd, J=8.1, 12.0 Hz), 7.16(1H, t, J=6.6 Hz), 7.20-7.29(5H, m), 8.19(2H, s). MS(m/z):425(M$^+$).

Example 52

Example 1 was repeated except that 4-(4-isobutylpiperazin-1-yl)phenol was replaced with 4-(2,5-difluoro-4-hydroxyphenyl)-1-(octylsulfonyl)piperazine (247 mg) and the resulting crude product was purified on TLC (developer, chloroform: methanol=23:1), to provide 2,5-difluoro-4-[4-(octylsulfonyl)piperazin-1-yl]phenyl-O-sulfamate (192 mg).

$^1$H-NMR(CDCl$_3$, δ):0.88(3H, t, J=6.9 Hz), 1.18-1.38(8H, m), 1.38-1.50(2H, m), 1.78-1.90(2H, m), 2.90-3.00(2H, m), 3.10-3.22(4H, m), 6.77(1H, dd, J=7.7, 11.6 Hz), 7.19(1H, dd, J=7.1, 11.8 Hz). MS(m/z):469(M$^+$).

Example 53

Example 1 was repeated except that 4-(4-isobutylpiperazin-1-yl)phenol was replaced with 4-(2,5-difluoro-4-hydroxyphenyl)-1-(2,4,6-trimethylphenylsulfonyl)piperazine (124 mg) and the resulting crude product was purified on TLC (developer, chloroform: methanol=24:1), to provide 2,5-difluoro-4-[4-(1,3,5-trimethylphenylsulfonyl)-piperazin-1-yl]phenyl-O-sulfamate (119 mg).

$^1$H-NMR(CDCl$_3$, δ):2.32(3H, s), 2.64(6H, s), 3.06-3.16 (4H, m), 3.28-3.42(4H, m), 5.18(2H, s), 6.72(1H, dd, J=7.7, 12.0 Hz), 6.98(2H, s), 7.16(1H, dd, J=6.9, 12.0 Hz). MS(m/z):475(M$^+$).

Example 54

Example 1 was repeated except that 4-(4-isobutylpiperazin-1-yl)phenol was replaced with 4-(2,5-difluoro-4-hydroxyphenyl)-1-(4-fluorophenylsulfonyl)piperazine (207 mg) and the resulting crude product was purified on TLC (developer, chloroform: methanol=20:1), to provide 2,5-difluoro-4-[4-(4-fluorophenylsulfonyl)piperazin-1-yl]-phenyl-O-sulfamate (201 mg).

$^1$H-NMR(CDCl$_3$, δ):3.10-3.27(8H, m), 5.13(2H, s), 6.72 (1H, dd, J=7.7, 11.6 Hz), 7.13(1H, dd, J=7.1, 11.7 Hz), 7.21-7.30(2H, m), 7.78-7.88(2H, m). MS(m/z):451(M$^+$).

Example 55

Example 1 was repeated except that 4-(4-isobutylpiperazin-1-yl)phenol was replaced with 1-(4-chlorophenylsulfonyl)-4-(2,5-difluorophenyl)piperazine (150 mg) and the resulting crude product was purified on TLC (developer, chloroform: methanol=10:1), to provide 4-[4-(4-chlorophenylsulfonyl)piperazin-1-yl]-2,5-difluorophenyl-O-sulfamate (175 mg).

$^1$H-NMR(DMSO-d$_6$, δ):3.0-3.2(8H, m), 7.12(1H, dd, J=8.1, 11.9 Hz), 7.24(1H, dd, J=7.3, 12.7 Hz), 7.76, 7.79(4H, AB, J=8.9 Hz), 8.20(2H, s). MS(m/z):467(M$^+$).

Example 56

Example 1 was repeated except that 4-(4-isobutylpiperazin-1-yl)phenol was replaced with 1-(4-chlorobenzylsulfonyl)-4-(2,5-difluoro-4-hydroxyphenyl)piperazine (380 mg) and the resulting crude product was purified on TLC (developer, ethyl acetate: hexane=1:1), to provide 4-[(4-chlorobenzylsulfonyl)piperazin-1-yl]-2,5-difluorophenyl-O-sulfamate (144 mg).

$^1$H-NMR(DMSO-d$_6$, δ):3.0-3.1(4H, m), 3.2-3.3(4H, m), 4.49(2H, s), 7.07-7.14(1H, m), 7.23-7.30(1H, m), 7.43-7.49 (4H, m), 8.19(2H, br s). MS(m/z):481(M$^+$), 402, 213.

Example 57

Example 1 was repeated except that 4-(4-isobutylpiperazin-1-yl)phenol was replaced with 4-(2,5-difluoro-4-hydroxyphenyl)-1-phenethylsulfonylpiperazine (150 mg) and the resulting crude product was purified on TLC (developer, chloroform: methanol=20:1), to provide 2,5-difluoro-4-(4-phenethylsulfonylpiperazin-1-yl)phenyl-O-sulfamate (166 mg).

$^1$H-NMR(DMSO-d$_6$, δ):2.9-3.5(12H, m), 7.1-7.3(7H, m), 8.20(2H, s). MS(m/z):461(M$^+$), 382, 213.

Example 58

4-[4-(3-Cyclohexylpropyl)piperazin-1-yl]-2,5-difluorophenyl-O-sulfamate (100 mg) was dissolved in 0.56 mL of tetrahydrofuran, and 30 μL of conc. hydrochloric acid was added to the resulting solution at room temperature. After 1.7 hours' stirring, precipitated crystals were recovered by filtration, washed with tetrahydrofuran (4 mL), and heat-dried under reduced pressure, to provide 4-[4-(3-cyclohexylpropyl)piperazin-1-yl]-2,5-difluorophenyl-O-sulfamate hydrochloride (52 mg).

$^1$H-NMR(DMSO-d$_6$, δ):0.82-0.96(2H, m), 1.07-1.31(6H, m), 1.58-1.80(7H, m), 3.01-3.27(6H, m), 3.43-3.64(4H, m), 7.22(1H, dd, J=8.1, 11.9 Hz), 7.31(1H, dd, J=7.1, 12.5 Hz), 8.24(2H, s). MS(m/z):417(M$^+$-xHCl).

Example 59

The 2,5-difluoro-4-[4-(3-phenylpropyl)piperidino]phenyl-O-sulfamate (205 mg) which was synthesized in Example 37 was dissolved in 3 mL of tert-butyl methyl ether, to which benzene-sulfonic acid monohydrate (102 mg) was added, followed by 30 minutes' stirring at room temperature. Thus precipitated crystals were recovered by filtration, washed with tert-butyl methyl ether (3 mL) and dried to provide crude crystals (251 mg) of 2,5-difluoro-4-[4-(3-phenylpropyl)piperidino]phenyl-O-sulfamate benzenesulfonate. The crude crystals (100 mg) was added to acetone (1 mL), heated under reflux, and after stopping the heating, heptane (0.7 mL) was added, followed by 70 minutes' stirring at room temperature. Thus precipitated crystals were recovered by filtration, washed with acetone-heptane mixed solution (1:1) (2 mL) and dried to provide crystalline 2,5-difluoro-4-[4-(3-phenylpropyl)piperidino]phenyl-O-sulfamate benzenesulfonate (58 mg).

$^1$H-NMR(CD$_3$OD, δ):1.32-1.43(2H, m), 1.52-1.76(5H, m), 2.00(2H, d, J=13.5 Hz), 2.63(2H, t, J=7.5 Hz), 3.38(2H, t, J=11.0 Hz), 3.65(2H, d, J=12.3 Hz), 7.10-7.29(5H, m), 7.36-7.46(3H, m), 7.49(1H, dd, J=6.8, 11.8 Hz), 7.60(1H, dd, J=7.3, 10.8 Hz), 7.78-7.87(2H, m).

Example 60

A solution of the 4-[4-(4-chlorophenylsulfonyl)piperazin-1-yl]-2,5-difluorophenyl-O-sulfamate (100 mg) which was synthesized in Example 55 in ethyl acetate (1.5 mL) was heated to 50° C., and to which 4N-hydrochloric acid/ethyl acetate (107 μL) was added, followed by 13 minutes' stirring at room temperature. Whereupon precipitated crystals were recovered by filtration, washed with ethyl acetate-heptane mixed solution (1:1) (2 mL) and dried to provide 4-[4-(4-chlorophenylsulfonyl, piperazin-1-yl]-2,5-difluorophenyl-O-sulfamate hydrochloride (61 mg).

$^1$H-NMR(CD$_3$OD, δ):3.15(8H, br s), 6.95(1H, dd, J=7.9, 11.8 Hz), 7.16(1H, dd, J=7.3, 12.3 Hz), 7.79(4H, AB, J=8.7 Hz).

Production Example 1

To a mixture of 1-(4-methoxyphenyl)piperazine dihydrochloride (264 mg), tetrahydrofuran (1.3 mL) and potassium carbonate (304 mg), (2-bromoethyl)benzene (150 μL) was added under cooling with ice, followed by 4.5 hours' heating under reflux. The reaction mixture was poured in saturated saline solution, and the product was extracted with ethyl acetate. The organic layer was washed with saturated saline solution and dried over anhydrous magnesium sulfate. Distilling the solvent off, crude product (268 mg) of 1-(4-methoxyphenyl)-4-phenethylpiperazine was obtained.

$^1$H-NMR(CDCl$_3$, δ):2.60-2.78(6H, m), 2.80-2.91(2H, m), 3.08-3.20(4H, m), 3.78(3H, s), 6.83(2H, d, J=9.3 Hz), 6.91 (2H, d, J-9.3 Hz), 7.17-7.37(5H, m). MS(m/z):296(M$^+$).

Production Example 2

To a solution of 1-(4-methoxyphenyl)-4-phenethylpiperazine (165 mg) in 1,2-dichloroethane (1.5 mL), boron tribromide (132 μL) was added under cooling with ice. The temperature was raised to the ambient level, followed by 3 hours' stirring. The reaction mixture was poured in saturated saline solution, rendered weakly alkaline with saturated aqueous sodium hydrogencarbonate solution, and the product was extracted with ethyl acetate. The organic layer was washed with saturated saline solution and dried over anhydrous magnesium sulfate. Distilling the solvent off, the crude product recovered was purified on TLC (developer, chloroform: methanol=15:1) to provide 4-(4-phenethylpiperazin-1-yl)phenol (28 mg).

$^1$H-NMR(DMSO-d$_6$, δ):2.43-2.50(2H, m), 2.57(4H, br s), 2.74(2H, t, J=7.7 Hz), 2.94(4H, br s), 6.62(2H, d, J=8.9 Hz), 6.77(2H, d, J=8.9 Hz), 7.12-7.30(5H, m), 8.75(1H, s). MS(m/z):282(M$^+$).

Production Example 3

To 1-(4-methoxyphenyl)piperazine dihydrochloride (264 mg), pyridine (2.6 mL) and isovaleryl chloride (134 μL) were added, followed by 2.4 hours' stirring. The reaction mixture was poured in aqueous sodium hydrogencarbonate solution and the product was extracted with ethyl acetate. The organic layer was washed with saturated saline solution and dried over anhydrous magnesium sulfate. Distilling the solvent off, crude 1-isovaleryl-4-(4-methoxyphenyl)piperazine (138 mg) was obtained.

Production Example 4

Production Example 2 was repeated except that 1-(4-methoxyphenyl)-4-phenethylpiperazine was replaced with 1-isovaleryl-4-(4-methoxyphenyl)piperazine (138 mg), to provide crude product (124 mg) of 4-(4-hydroxyphenyl)-1-isovalerylpiperazine.

Production Example 5

Production Example 3 was repeated except that isovaleryl chloride was replaced with benzoyl chloride (128 μL), to provide crude 1-benzoyl-4-(4-methoxyphenyl)piperazine (199 mg).

$^1$H-NMR(CDCl$_3$, δ):2.90-3.25(4H, m), 3.50-3.73(2H, m), 3.78-4.07(2H, m), 6.83(2H, d, J=9.3 Hz), 6.90(2H, d, J=9.3 Hz), 7.43(5H, s). MS(m/z):296(M$^+$).

Production Example 6

Production Example 2 was repeated except that 1-(4-methoxyphenyl)-4-phenethylpiperazine was replaced with 1-benzoyl-4-(4-methoxyphenyl)piperazine (193 mg), and the resulting crude product was purified on TLC (developer, chloroform: acetone=4:1) to provide 1-benzoyl-4-(4-hydroxyphenyl)piperazine (141 mg).

$^1$H-NMR(DMSO-d$_6$, δ):2.94(4H, br s), 3.30-3.82(4H, m), 6.63(2H, d, J=8.9 Hz), 6.79(2H, d, J=8.9 Hz), 7.33-7.50(5H, m), 8.82(1H, s). MS(m/z):282(M$^+$).

Production Example 7

To a solution of 4-chlorobenzeneacetyl chloride (378 mg) in N,N-dimethylacetamide (2 mL), 4-(piperazin-1-yl)phenol (356 mg) was added under cooling with ice, followed by 2 hours' stirring at room temperature. The reaction mixture was poured in saturated saline solution, and to which diluted hydrochloric acid was added. The product was extracted with ethyl acetate-tetrahydrofuran (1:1), and the organic layer was washed with saturated saline solution and dried over anhydrous magnesium sulfate. Distilling the solvent off, crude 1-(4-chlorophenylacetyl)-4-(4-hydroxyphenyl)piperazine (421 mg) was obtained.

$^1$H-NMR(DMSO-d$_6$, δ):2.88(4H, br s), 3.58(4H, br s), 3.75(2H, s), 6.63(2H, d, J=8.9 Hz), 6.79(2H, d, J=8.9 Hz), 7.24(2H, d, J=8.5 Hz), 7.36(2H, d, J=8.5 Hz), 8.85(1H, br s). MS(m/z):332(M$^+$+2), 330(M$^+$).

Production Example 8

Production Example 7 was repeated except that 4-chlorobenzeneacetyl chloride was replaced with benzylsulfonyl chloride (381 mg) to provide crude 1-benzylsulfonyl-4-(4-hydroxyphenyl)piperazine (200 mg).

$^1$H-NMR(DMSO-d$_6$, δ):2.99(4H, br s), 3.13-3.30(4H, m), 4.45(2H, s), 6.65(2H, d, J=8.9 Hz), 6.73-6.94(2H, m), 7.28-7.50(5H, m). MS(m/z):332(M$^+$).

Production Example 9

A mixture of 5-bromo-2-methoxytoluene (402 mg), 1-(2-phenethyl)piperazine (1.142 g), sodium tert-butoxide (270 mg), (R)-BINAP (38 mg), tris(dibenzylideneacetone) dipalladium (0)(15 mg) and toluene (20 mL) was heated under reflux for 10.6 hours in nitrogen atmosphere. The reaction mixture was poured in saturated saline solution, and the product was extracted with ethyl acetate. The organic layer was washed with water and dried over anhydrous magnesium sulfate. The solvent was distilled off and the remaining crude product was purified on silica gel column chromatography (eluent, chloroform: acetone=12:1) to provide 1-(4-methoxy-3-methylphenyl)-4-phenethylpiperazine (338 mg).

$^1$H-NMR(CDCl$_3$, δ):2.60-2.74(6H, m), 2.80-2.90(2H, m), 3.07-3.16(4H, m), 3.78(3H, s), 6.76(2H, s), 6.81(1H, s), 7.17-7.37(5H, m). MS(m/z):310(M$^+$).

Production Example 10

A mixture of 1-(4-methoxy-3-methylphenyl)-4-phenethyl-piperazine (327 mg) and pyridinium chloride (731 mg) was heated to 210° C. and stirred for an hour. The reaction liquid was diluted with 1 mL of toluene, and to which saturated saline solution was added. Further adding saturated aqueous sodium hydrogencarbonate solution to render the system weakly alkaline, the product was extracted with ethyl acetate-tetrahydrofuran (1:1). The organic layer was washed with saturated saline solution and dried over anhydrous magnesium sulfate. The solvent was distilled off and the remaining crude product was purified on TLC (developer, chloroform: methanol=15:1) to provide 2-methyl-4-(4-phenethylpiperazin-1-yl)phenol (141 mg).

$^1$H-NMR(CDCl$_3$, δ):2.61-2.79(6H, m), 2.79-2.91(2H, m), 3.06-3.20(4H, m), 6.69(2H, s), 6.77(1H, s), 7.16-7.37(5H, m). MS(m/z):296(M$^+$).

Production Example 11

Production Example 9 was repeated except that 5-bromo-2-methoxytoluene was replaced with 2-bromo-5-methoxytoluene (402 mg) to provide 1-(4-methoxy-2-methylphenyl)-4-phenethylpiperazine (523 mg).

$^1$H-NMR(CDCl$_3$, δ):2.58-2.79(6H, m), 2.79-2.88(2H, m), 2.88-2.96(4H, m), 3.78(3H, s), 6.70(1H, dd, J=2.9, 8.7 Hz), 6.76(1H, d, J=3.1 Hz), 7.00(1H, d, J=8.5 Hz), 7.16-7.36(5H, m). MS(m/z):310(M$^+$).

Production Example 12

Production Example 10 was repeated except that 1-(4-methoxy-3-methylphenyl)-4-phenethylpiperazine was replaced with 1-(4-methoxy-2-methylphenyl)-4-phenethylpiperazine (512 mg), and the resulting crude product was purified on TLC (developer, chloroform: methanol=15:1) to provide 3-methyl-4-(4-phenethyl-piperazin-1-yl)phenol (417 mg).

$^1$H-NMR(CDCl$_3$, δ):2.60-2.82(6H, m), 2.82-3.00(6H, m), 6.62(1H, dd, J=2.7, 8.5 Hz), 6.69(1H, d, J=2.7 Hz), 6.95(1H, d, J=8.5 Hz), 7.18-7.37(5H, m). MS(m/z):296(M$^+$).

Production Example 13

A mixture of 2-fluoro-5-methoxybenzonitrile (400 mg), N,N-dimethylacetamide (5.2 mL), potassium carbonate (878 mg) and 4-phenylpiperidine (1.026 g) was heated for 14 hours at 110° C., 5 hours at 130° C., and further 2.7 hours at 150° C.

The reaction mixture was poured in saturated saline solution, and the product was extracted with ethyl acetate. The organic layer was washed with saturated saline solution and dried over anhydrous magnesium sulfate. The solvent was distilled off and the remaining crude product was purified on silica gel column chromatography (eluent, hexane: ethyl acetate=6:1) to provide 5-methoxy-2-(4-phenylpiperidino) benzonitrile (343 mg).

$^1$H-NMR(CDCl$_3$, δ):1.92-2.11(4H, m), 2.58-2.70(1H, m), 2.88(2H, dt, J=2.9, 11.7 Hz), 3.55(2H, d, J=11.7 Hz), 3.79(3H, s), 7.02-7.37(8H, m). MS(m/z):292(M$^+$).

Production Example 14

Production Example 10 was repeated except that 1-(4-methoxy-3-methylphenyl)-4-phenethylpiperazine was replaced with 5-methoxy-2-(4-phenylpiperidino)benzonitrile (99 mg), and the resulting crude product was purified on TLC (developer, hexane: ethyl acetate=2:1) to provide 5-hydroxy-2-(4-phenylpiperidino)benzonitrile (42 mg).

$^1$H-NMR(DMSO-d$_6$, δ):1.72-1.92(4H, m), 2.58-2.70(1H, m), 2.80(2H, t, J=11.6 Hz), 3.37(2H, d, J=12.0 Hz), 6.97-7.36 (8H, m), 9.67(1H, s). MS(m/z):278(M$^+$).

Production Example 15

Production Example 13 was repeated except that 4-phenylpiperidine was replaced with 4-benzylpiperidine (1.1 mL), to provide 2-(4-benzylpiperidino)-5-methoxybenzonitrile (280 mg).

$^1$H-NMR(CDCl$_3$, δ):1.47-1.70(3H, m), 1.77(2H, d, J=12.5 Hz), 2.60(2H, d, J=7.0 Hz), 2.67(2H, t, J=11.1 Hz), 3.39(2H, d, J=12.1 Hz), 3.78(3H, s), 6.92-7.34(8H, m). MS(m/z):306 (M$^+$).

Production Example 16

Production Example 10 was repeated except that 1-(4-methoxy-3-methylphenyl)-4-phenethylpiperazine was replaced with 2-(4-benzylpiperidino)-5-methoxybenzonitrile (99 mg), and the resulting crude product was purified on TLC (developer, hexane: ethyl acetate=2:1) to provide 2-(4-benzylpiperidino)-5-hydroxy-benzonitrile (40 mg).

$^1$H-NMR(DMSO-d$_6$, δ):1.27-1.43(2H, m), 1.52-1.70(3H, m), 2.56-2.63(4H, m), 3.21(2H, d, J=11.6 Hz), 6.93-7.05(3H, m), 7.08-7.22(3H, m), 7.22-7.33(2H, m), 9.63(1H, s). MS(m/z):292(M$^+$).

Production Example 17

Production Example 13 was repeated except that 4-phenylpiperidine was replaced with 4-(3-phenylpropyl)piperidine (1.115 g), to provide 5-methoxy-2-[4-(3-phenylpropyl) piperidino]-benzonitrile (291 mg).

$^1$H-NMR(CDCl$_3$, δ):1.31-1.53(5H, m), 1.60-1.76(2H, m), 1.80(2H, d, J=11.6 Hz), 2.62(2H, t, J=7.7 Hz), 2.68(2H, t, J=11.6 Hz), 3.40(2H, d, J=12.0 Hz), 2.79(3H, s), 6.97(1H, d, J=8.9 Hz), 6.99-7.35(7H, m). MS(m/z):334(M$^+$).

Production Example 18

Production Example 10 was repeated except that 1-(4-methoxy-3-methylphenyl)-4-phenethylpiperazine was replaced with 5-methoxy-2-[4-(3-phenylpropyl)piperidino] benzonitrile (290 mg), and the resulting crude product was purified on TLC (developer, hexane: ethyl acetate=3:1) to provide 5-hydroxy-2-[4-(3-phenyl-propyl)piperidino]benzonitrile (145 mg).

$^1$H-NMR(CDCl$_3$, δ):1.29-1.55(5H, m), 1.62-1.73(2H, m), 1.79(2H, d, J=12.3 Hz), 2.62(2H, t, J=7.7 Hz), 2.68(2H, t, J=11.9 Hz), 3.39(2H, d, J=11.9 Hz), 4.88(1H, s), 6.89-7.33 (8H, m). MS(m/z):320(M$^+$).

Production Example 19

Production Example 13 was repeated except that 4-phenylpiperidine was replaced with piperazine dihydrochloride (7.036 g) (6 equivalents), to provide 5-methoxy-2-(piperazin-1-yl)-benzonitrile (485 mg).

$^1$H-NMR(CDCl$_3$, δ):3.04-3.15(8H, m), 3.78(3H, s), 7.00 (1H, d, J=8.5 Hz), 7.04-7.11(2H, m). MS(m/z):217(M$^+$).

Production Example 20

Production Example 1 was repeated except that 1-(4-methoxyphenyl)piperazine dihydrochloride was replaced with 5-methoxy-2-(piperazin-1-yl)benzonitrile (483 mg), to provide crude 5-methoxy-2-(4-phenethylpiperazin-1-yl)benzonitrile (739 mg).

Production Example 21

Production Example 10 was repeated except that 1-(4-methoxy-3-methylphenyl)-4-phenethylpiperazine was replaced with 5-methoxy-2-(4-phenethylpiperazin-1-yl)benzonitrile (257 mg), and the resulting crude product was purified on TLC (developer, chloroform: methanol=12:1) to provide 5-hydroxy-2-(4-phenethyl-piperazin-1-yl)benzonitrile (124 mg).

$^1$H-NMR(CDCl$_3$, δ):2.66-2.90(8H, m), 3.07-3.22(4H, m), 6.92-7.08(3H, m), 7.17-7.36(5H, m). MS(m/z):307(M$^+$).

Production Example 22

Production Example 1 was repeated except that 1-(4-methoxyphenyl)piperazine dihydrochloride, (2-bromoethyl)benzene and tetrahydrofuran were replaced with 5-methoxy-2-(piperazin-1-yl)benzonitrile (599 mg), 3-cyclohexylpropyl methylsulfonate (608 mg) and N,N-dimethylformamide (6.8 mL), respectively, and the resulting crude product was purified on silica gel column chromatograpy (eluent, ethyl acetate: hexane=1:1) to provide 2-[4-(3-cyclohexylpropyl) piperazin-1-yl]-5-methoxybenzonitrile (439 mg).

$^1$H-NMR(CDCl$_3$, δ):0.80-0.96(2H, m), 1.08-1.28(6H, m), 1.46-1.77(7H, m), 2.39(2H, t, J=7.9 Hz), 2.67(4H, br s), 3.07-3.17(4H, m), 3.79(3H, s), 6.99(1H, d, J=8.5 Hz), 7.02-7.08 (2H, m). MS(m/z):341(M$^+$).

Production Example 23

Production Example 10 was repeated except that 1-(4-methoxy-3-methylphenyl)-4-phenethylpiperazine was replaced with 2-[4-(3-cyclohexylpropyl)piperazin-1-yl]-5-methoxybenzonitrile (430 mg), and the resulting crude product was purified on TLC (developer, chloroform: methanol=10:1) to provide 2-[4-(3-cyclohexylpropyl)piperazin-1-yl]-5-hydroxybenzonitrile (256 mg).

$^1$H-NMR(CDCl$_3$, δ):0.79-0.95(2H, m), 1.07-1.29(6H, m), 1.47-1.58(2H, m), 1.58-1.75(5H, m), 2.40(2H, t, J=7.9 Hz), 2.68(4H, br s), 3.05-3.18(4H, m), 6.89-7.04(3H, m). MS(m/z):327(M$^+$).

Production Example 24

A mixture of 2-chloro-4-nitrophenol (2.761 g), chloromethyl methyl ether (2.4 mL), acetone (16 mL) and potassium carbonate (3.1 g) was heated under reflux for 5 hours. The reaction mixture was poured in saturated saline solution, and the product was extracted with diethyl ether. The organic layer was washed with saturated saline solution, dried over anhydrous magnesium sulfate, and the solvent was distilled off, to provide crude 2-chloro-1-methoxy-methoxy-4-nitrobenzene (3.091 g).

$^1$H-NMR(CDCl$_3$, δ):3.53(3H, s), 5.37(2H, s), 7.27(1H, d, J=9.3 Hz), 8.13(1H, dd, J=2.7, 9.3 Hz), 8.31(1H, d, J=2.7 Hz). MS(m/z):219(M$^+$+2), 217(M$^+$).

Production Example 25

A mixture of 2-chloro-1-methoxymethoxy-4-nitrobenzene (3.091 g), ethyl acetate (40 mL), ethanol (40 mL) and 5% palladium-on-carbon (158 mg) was stirred for 22 hours under normal pressure in hydrogen atmosphere. The insoluble matter was removed by filtration. Distilling the filtrate off, crude 3-chloro-4-methoxymethoxy-aniline (2.588 g) was obtained.

$^1$H-NMR(CDCl$_3$, δ):3.53(3H, s), 5.22(2H, s), 6.55(1H, dd, J=2.7, 8.9 Hz), 6.76(1H, d, J=2.7 Hz), 6.98(1H, d, J=8.9 Hz). MS(m/z):189(M$^+$+2), 187(M$^+$).

Production Example 26

A mixture of 3-chloro-4-methoxymethoxyaniline (2.197 g), bis(2-chloroethyl)amine hydrochloride (2.092 g), sodium carbonate (2.485 g) and ethanol (13 mL) was heated under reflux for 22 hours. The reaction mixture was poured in saturated saline solution and the product was extracted with ethyl acetate-tetrahydrofuran (1:1). The organic layer was washed with saturated saline solution and dried over anhydrous magnesium sulfate. Distilling the solvent off, crude 1-(3-chloro-4-methoxymethoxyphenyl)piperazine (2.914 g) was obtained.

Production Example 27

Production Example 1 was repeated except that 1-(4-methoxyphenyl)piperazine dihydrochloride was replaced with 1-(3-chloro-4-methoxymethoxyphenyl)piperazine (924 mg). The resulting crude product was purified on silica gel column chromatography (eluent, chloroform: acetone=8:1) to provide 1-(3-chloro-4-methoxymethoxyphenyl)-4-phenethylpiperazine (217 mg).

$^1$H-NMR(CDCl$_3$, δ):2.60-2.78(6H, m), 2.78-2.90(2H, m), 3.10-3.22(4H, m), 3.52(3H, s), 5.22(2H, s), 6.52(1H, dd, J=2.7, 8.5 Hz), 6.72(1H, d, J=2.7 Hz), 6.77(1H, dd, J=2.7, 8.9 Hz), 7.13-7.38(5H, m). MS(m/z):362(M$^+$+2), 360(M$^+$).

Production Example 28

To 1-(3-chloro-4-methoxymethoxyphenyl)-4-phenethylpiperazine (214 mg), 2-propanol (1 mL) and tetrahydrofuran (1 mL) were added, followed by cooling with ice and addition of conc. hydrochloric acid (0.5 mL). Raising the temperature back to the ambient level, the mixture was stirred for 4.5 hours. The reaction mixture was poured in saturated saline solution, rendered weakly alkaline with saturated aqueous sodium hydrogencarbonate solution, and the product was extracted with ethyl acetate. The organic layer was washed with saturated saline solution and dried over anhydrous magnesium sulfate. The solvent was distilled off and the resulting crude product was purified on TLC (developer, chloroform: acetone=5:1) to provide 2-chloro-4-(4-phenethylpiperazin-1-yl)phenol (93 mg).

$^1$H-NMR(DMSO-d$_6$, δ):2.47-2.62(6H, m), 2.73(2H, t, J=7.9 Hz), 2.91-3.00(4H, m), 6.74(1H, dd, J=2.7, 8.9 Hz), 6.82(1H, d, J=8.5 Hz), 6.83(1H, d, J=3.1 Hz), 7.12-7.30(5H, m), 9.38(1H, s). MS(m/z):318(M$^+$+2), 316(M$^+$).

Production Example 29

Production Example 9 was repeated except that 5-bromo-2-methoxytoluene was replaced with 1-benzyloxy-4-bromo-2-chlorobenzene (861 mg), and 1-phenethylpiperazine was replaced with 1-(3-cyclohexylpropyl)piperazine (730 mg). Whereby obtained crude product was purified on silica gel column chromatography (eluent, chloroform: methanol=10:1) to provide 1-(4-benzyloxy-3-chlorophenyl)-4-(3-cyclohexylpropyl)piperazine (1.24 g).

$^1$H-NMR(CDCl$_3$, δ):0.88(2H, m), 1.1-1.3(6H, m), 1.4-1.8 (7H, m), 2.35(2H, m), 2.58(4H, br t, J=5.0 Hz), 3.10(4H, br t, J=4.6 Hz), 5.08(2H, s), 6.73(1H, dd, J=2.7, 8.9 Hz), 6.88(1H, d, J=8.9 Hz), 6.98(1H, d, J=2.7 Hz), 7.26-7.47(5H, m). MS(m/z):426(M$^+$).

Production Example 30

1-(4-Benzyloxy-3-chlorophenyl)-4-(3-cyclohexylpropyl)-piperazine (1.21 g) was suspended in acetic acid (6.0 mL), and to the suspension conc. hydrochloric acid (2.83 mL) was added, followed by 2 hours' heating under reflux. Allowing the system to cool off, the solvent was distilled off under reduced pressure, and the remaining crystals were washed with acetone and dried under reduced pressure at 60° C., to provide 2-chloro-4-[4-(3-cyclohexylpropyl)piperazin-1-yl]-phenol hydrochloride (760 mg).

$^1$H-NMR(CD$_3$OD, δ):0.95(2H, m), 1.1-1.4(6H, m), 1.6-1.9(7H, m), 3.19(2H, m), 3.71(4H, br s), 6.92(1H, d, J=8.9 Hz), 7.04(1H, dd, J=3.1, 8.9 Hz), 7.23(1H, d, J=2.7 Hz). MS(m/z):336(M$^+$-xHCl).

Production Example 31

Production Example 1 was repeated except that 1-(4-methoxyphenyl)piperazine dihydrochloride and (2-bromoethyl)-benzene were replaced with 1-(3-chloro-4-methoxymethoxyphenyl)-piperazine (924 mg) and 2-bromoacetophenone (789 mg), respectively. Thus obtained crude product was purified on silica gel column chromatography (eluent, chloroform: acetone=20:1), to provide 2-[4-(3-chloro-4-methoxymethoxyphenyl)piperazin-1-yl]-1-phenylethan-1-one (225 mg).

$^1$H-NMR(CDCl$_3$, δ):2.74-2.85(4H, m), 3.16-3.26(4H, m), 3.52(3H, s), 5.15(2H, s), 6.78(1H, dd, J=3.1, 8.9 Hz), 6.96

(1H, d, J=2.7 Hz), 7.08(1H, d, J=8.9 Hz), 7.48(2H, t, J=7.7 Hz), 7.58(1H, t, J=6.2 Hz), 8.03(2H, d, J=8.5 Hz). MS(m/z): 376($M^+$+2), 374($M^+$).

Production Example 32

Production Example 28 was repeated except that 1-(3-chloro-4-methoxymethoxyphenyl)-4-phenethylpiperazine was replaced with 2-[4-(3-chloro-4-methoxymethoxyphenyl)piperazin-1-yl]-1-phenylethan-1-one (221 mg). Thus obtained crude product was purified on TLC (developer, chloroform: acetone=6:1) to provide 2-[4-(3-chloro-4-hydroxyphenyl)piperazin-1-yl]-1-phenylethan-1-one (26 mg).
$^1$H-NMR(DMSO-$d_6$, δ):2.65(4H, br s), 2.99(4H, br s), 3.89(2H, br s), 6.73(1H, dd, J=2.7, 8.9 Hz), 6.80(1H, d, J=8.9 Hz), 6.86(1H, d, J=2.7 Hz), 7.50(2H, t, J=7.7 Hz), 7.59-7.67 (1H, m), 7.98(2H, d, J=8.5 Hz), 9.38(1H, s). MS(m/z):332 ($M^+$+2), 330($M^+$).

Production Example 33

Production Example 9 was repeated except that 5-bromo-2-methoxytoluene and 1-(2-phenethyl)piperazine were replaced with 1-benzyloxy-4-bromo-2-chlorobenzene (7.138 g) and piperazine (12.404 g), respectively. Thus obtained crude product was purified on silica gel column chromatography (eluent, chloroform: methanol=5:2) to provide 1-(4-benzyloxy-3-chlorophenyl)piperazine (4.739 g).
$^1$H-NMR(CDCl$_3$, δ):2.90-3.15(8H, m), 5.10(2H, s), 6.75 (1H, dd, J=2.9, 9.1 Hz), 6.89(1H, d, J=8.9 Hz), 6.98(1H, d, J=3.1 Hz), 7.28-7.50(5H, m). MS(m/z):304($M^+$+2), 302($M^+$).

Production Example 34

To 1-(4-benzyloxy-3-chlorophenyl)piperazine (4.739 g), acetic acid (20 mL) and conc. hydrochloric acid (10 mL) were added, followed by 1.5 hours' heating under reflux. The reaction liquid was let stand to cool off, and from which the solvent was distilled off by heating under reduced pressure. The crude product was suspended in tetrahydrofuran, recovered by filtration, washed with tetrahydrofuran and dried by heating under reduced pressure to provide 2-chloro-4-(piperazin-1-yl)phenol hydrochloride (4.050 g).

Production Example 35

To a mixture of 4-bromo-3-chlorophenol (2.5 g), potassium carbonate (2.165 g) and N,N-dimethylformamide (26 mL), benzyl chloride (1.8 mL) was added under cooling with ice. Raising the temperature to the ambient level, the system was stirred for 23 hours. The reaction mixture was poured in saturated saline solution and the product was extracted with ethyl acetate. The organic layer was washed with saturated saline solution, and dried over anhydrous magnesium sulfate. Distilling the solvent off, the remaining crude product was purified on silica gel column chromatography (eluent, hexane: ethyl acetate=10:1) to provide 4-benzyloxy-1-bromo-2-chlorobenzene (3.029 g).
$^1$H-NMR(CDCl$_3$, δ):5.02(2H, s), 6.75(1H, dd, J=2.7, 8.9 Hz), 7.08(1H, d, J=2.7 Hz), 7.28-7.42(5H, m), 7.45(1H, d, J=8.9 Hz). MS(m/z):298($M^+$+2), 296($M^+$).

Production Example 36

Production Example 9 was repeated except that 5-bromo-2-methoxytoluene was replaced with 4-benzyloxy-1-bromo-2-chlorobenzene (595 mg). Thus obtained crude product was purified on silica gel column chromatography (eluent, chloroform: acetone=10:1) to provide 1-(4-benzyloxy-2-chlorophenyl)-4-phenethylpiperazine (67 mg).
$^1$H-NMR(CDCl$_3$, δ):2.61-2.80(6H, m), 2.80-2.89(2H, m), 3.03(4H, br s), 5.00(2H, s), 6.83(1H, dd, J=2.7, 8.9 Hz), 7.01(1H, d, J=8.9 Hz), 7.03(1H, d, J=3.1 Hz), 7.14-7.47(10H, m). MS(m/z):408($M^+$+2), 406($M^+$).

Production Example 37

Production Example 30 was repeated except that 1-(4-benzyloxy-3-chlorophenyl)-4-(3-cyclohexylpropyl)piperazine was replaced with 1-(4-benzyloxy-2-chlorophenyl)-4-phenethylpiperazine (65 mg). Thus obtained crude product was purified on TLC (developer, chloroform: methanol=17:1) to provide 3-chloro-4-(4-phenethylpiperazin-1-yl)phenol (29 mg).
$^1$H-NMR(CDCl$_3$, δ):2.63-2.80(6H, m), 2.80-2.89(2H, m), 3.03(4H, br s), 6.69(1H, dd, J=2.9, 8.8 Hz), 6.90(1H, d, J=2.9 Hz), 6.96(1H, d, J=8.8 Hz), 7.18-7.37(5H, m). MS(m/z):318 ($M^+$+2), 316($M^+$).

Production Example 38

A mixture of 1-(4-benzyloxy-3-fluorophenyl)piperazine (286 mg), potassium carbonate (138 mg), sodium iodide (225 mg), N,N-dimethylformamide (2.5 mL) and n-octyl bromide (173 μL) was stirred for 2 hours under heating at 100° C. The reaction mixture was poured in saturated saline solution, and the product was extracted with ethyl acetate. The organic layer was washed with saturated saline solution and dried over anhydrous magnesium sulfate. Distilling the solvent off, crude 1-(4-benzyloxy-3-fluorophenyl)-4-octylpiperazine (369 mg) was obtained.
$^1$H-NMR(CDCl$_3$, δ):0.89(3H, t, J=6.9 Hz), 1.15-1.38 (10H, m), 1.40-1.62(2H, m), 2.39(2H, t, J=7.7 Hz), 2.47-2.67 (4H, m), 3.03-3.20(4H, m), 5.07(2H, s), 6.57(1H, dd, J=2.7, 8.9 Hz), 6.71(1H, dd, J=3.1, 13.9 Hz), 6.91(1H, t, J=9.1 Hz), 7.28-7.47(5H, m). MS(m/z):398($M^+$).

Production Example 39

Production Example 30 was repeated except that 1-(4-benzyloxy-3-chlorophenyl)-4-(3-cyclohexylpropyl)piperazine was replaced with 1-(4-benzyloxy-3-fluorophenyl)-4-octylpiperazine (365 mg), to provided crude 2-fluoro-4-(4-octylpiperazin-1-yl)phenol (252 mg).
$^1$H-NMR(CDCl$_3$, δ): 0.87(3H, t, J=7.0 Hz), 1.13-1.39 (10H, m), 1.43-1.62(2H, m), 2.41(2H, t, J=7.9 Hz), 2.63(4H, br s), 3.00-3.20(4H, m), 6.59(1H, dd, J=2.7, 8.9 Hz), 6.65(1H, dd, J=2.9, 13.3 Hz), 6.88(1H, t, J=9.5 Hz). MS(m/z):308 ($M^+$).

Production Example 40

Production Example 1 was repeated except that 1-(4-methoxyphenyl)piperazine dihydrochloride and (2-bromoethyl)-benzene were replaced with 1-(3-fluoro-4-methoxyphenyl) piperazine (456 mg) and 2-cyclohexylethyl bromide (377 μL), respectively. Thus obtained crude product was purified on silica gel column chromatography (eluent, chloroform: methanol=30:1) to provide 1-(2-cyclohexylethyl)-4-(3-fluoro-4-methoxyphenyl)piperazine (229 mg).
$^1$H-NMR(CDCl$_3$, δ):0.86-1.00(2H, m), 1.09-1.37(4H, m), 1.37-1.48(2H, m), 1.48-1.77(5H, m), 2.40(2H, t, J=8.0 Hz), 2.50-2.65(4H, m), 3.00-3.17(4H, m), 6.62(1H, dd, J=1.5, 8.9 Hz), 6.72(1H, dd, J=2.9, 14.1 Hz), 6.88(1H, t, J=9.3 Hz). MS(m/z):320(M+).

Production Example 41

Production Example 10 was repeated except that 1-(4-methoxy-3-methylphenyl)-4-phenethylpiperazine was replaced with 1-(2-cyclohexylethyl)-4-(3-fluoro-4-methoxyphenyl)piperazine (218 mg) and the resulting crude product was purified on TLC (developer, chloroform: methanol=18:1) to provide 4-[4-(2-cyclohexylethyl-piperazin-1-yl]-2-fluorophenol (77 mg).
$^1$H-NMR(CDCl$_3$, δ):0.83-1.00(2H, m), 1.08-1.33(4H, m), 1.33-1.48(2H, m), 1.48-1.80(5H, m), 2.40(2H, t, J=7.9 Hz), 2.50-2.67(4H, m), 3.02-3.13(4H, m), 6.59(1H, dd, J=2.7, 8.9 Hz), 6.68(1H, dd, J=2.7, 13.1 Hz), 6.88(1H, dd, J=8.9, 10.1 Hz). MS(m/z):306(M+).

Production Example 42

Production Example 26 was repeated except that 3-chloro-4-methoxymethoxyaniline was replaced with 3-fluoro-p-anisidine (1.412 g), to provide crude 1-(3-fluoro-4-methoxyphenyl)piperazine (1.986 g).

Production Example 43

Production Example 1 was repeated except that 1-(4-methoxyphenyl)piperazine dihydrochloride was replaced with 1-(3-fluoro-4-methoxyphenyl)piperazine (1 g). Thus obtained crude product was purified on silica gel column chromatography (eluent, chloroform: acetone=6:1) to provide 1-(3-fluoro-4-methoxyphenyl)-4-phenethylpiperazine (493 mg).
$^1$H-NMR(CDCl$_3$, δ):2.60-2.77(6H, m), 2.77-2.90(2H, m), 3.05-3.20(4H, m), 6.62(1H, dd, J=2.7, 8.9 Hz), 6.73(1H, dd, J=2.9, 14.1 Hz), 6.88(1H, t, J=9.3 Hz), 7.18-7.36(5H, m). MS(m/z):314(M+).

Production Example 44

Production Example 10 was repeated except that 1-(4-methoxy-3-methylphenyl)-4-phenethylpiperazine was replaced with 1-(3-fluoro-4-methoxyphenyl)-4-phenethylpiperazine (482 mg), and the resulting crude product was purified on TLC (developer, chloroform: methanol=17:1) to provide 2-fluoro-4-(4-phenethylpiperazin-1-yl)phenol (175 mg).
$^1$H-NMR(CDCl$_3$, δ):2.60-2.75(6H, m), 2.77-2.88(2H, m), 3.05-3.17(4H, m), 6.62(1H, dd, J=2.7, 8.9 Hz), 6.69(1H, d, J=13.5 Hz), 6.89(1H, dd, J=8.9, 9.6 Hz), 7.16-7.35(5H, m). MS(m/z):300(M+).

Production Example 45

Production Example 38 was repeated except that n-octyl bromide was replaced with 1-(2-bromoethyl)-4-chlorobenzene (235 mg), to provide crude 1-(4-benzyloxy-3-fluorophenyl)-4-[2-(4-chlorophenyl)ethyl]piperazine (377 mg).

Production Example 46

Production Example 30 was repeated except that 1-(4-benzyloxy-3-chlorophenyl)-4-(3-cyclohexylpropyl)piperazine was replaced with 1-(4-benzyloxy-3-fluorophenyl)-4-[2-(4-chlorophenyl)-ethyl]piperazine (373 mg), to provide crude 4-[4-[2-(4-chlorophenyl)-ethyl]piperazin-1-yl]-2-fluorophenol (257 mg).

Production Example 47

Production Example 1 was repeated except that 1-(4-methoxyphenyl)piperazine dihydrochloride and (2-bromoethyl)-benzene were replaced with 1-(4-benzyloxy-3-fluorophenyl) piperazine (368 mg) and 3-cyclopentylpropyl methanesulfonate (319 mg), respectively, to provide crude 1-(4-benzyloxy-3-fluorophenyl)-4-(3-cyclopentylpropyl) piperazine (505 mg).
$^1$H-NMR(CDCl$_3$, δ):1.08(2H, m), 1.32(2H, m), 1.4-1.7 (6H, m), 1.76(3H, m), 2.37(2H, t, J=7.1 Hz), 2.58(4H, t, J=5.0 Hz), 3.11(4H, t, J=5.0 Hz), 5.06(2H, s), 6.56(1H, ddd, J=1.2, 1.5, 8.9 Hz), 6.70(1H, dd, J=2.7, 13.9 Hz), 6.89(1H, t, J=9.2 Hz), 7.28-7.46(5H, m). MS(m/z):396(M+).

Production Example 48

Production Example 30 was repeated except that 1-(4-benzyloxy-3-chlorophenyl)-4-(3-cyclohexylpropyl)piperazine was replaced with 1-(4-benzyloxy-3-fluorophenyl)-4-(3-cyclopentylpropyl)-piperazine (494 mg), to provide 4-[4-(3-cyclo-pentylpropyl)piperazin-1-yl]-2-fluorophenol hydrochloride (398 mg).
$^1$H-NMR(CD$_3$OD, δ):1.16(2H, m), 1.42(2H, q, J=7.3 Hz), 1.51-1.71(4H, m), 1.78-1.89(5H, m), 3.1-3.6(6H, m), 3.32 (4H, br s), 6.81-7.06(3H, m). MS(m/z):306(M+-xHCl).

Production Example 49

Production Example 9 was repeated except that 5-bromo-2-methoxytoluene and 1-(2-phenylethyl)piperazine were replaced with 1-benzyloxy-4-bromo-2-fluorobenzene (1.42 g) and 1-(3-cyclo-hexylpropyl)piperazine (1.28 g), respectively, to provide crude 1-(4-benzyloxy-3-fluorophenyl)-4-(3-cyclohexylpropyl)piperazine (2.31 g).
$^1$H-NMR(CDCl$_3$, δ):0.81-1.76(15H, m), 2.35(2H, t, J=7.7 Hz), 2.58(4H, t, J=5.0 Hz), 3.11(4H, t, J=4.6 Hz), 5.06(2H, s), 6.56(1H, ddd, J=1.2, 2.7, 8.9 Hz), 6.70(1H, dd, J=2.7, 13.9 Hz), 6.89(1H, t, J=9.2 Hz), 7.28-7.47(5H, m). MS(m/z):410 (M+).

Production Example 50

Production Example 1 was repeated except that 1-(4-methoxyphenyl)piperazine dihydrochloride and (2-bromoethyl)-benzene were replaced with 1-(4-benzyloxy-3-fluorophenyl) piperazine (1.33 g) and 3-cyclohexylpropyl methanesulfonate (1.02 g), respectively, to provide crude 1-(4-benzyloxy-3-fluorophenyl)-4-(3-cyclohexylpropyl) piperazine (1.89 g).

Production Example 51

Production Example 30 was repeated except that 1-(4-benzyloxy-3-chlorophenyl)-4-(3-cyclohexylpropyl)piperazine was replaced with 1-(4-benzyloxy-3-fluorophenyl)-4-(3-cyclohexylpropyl)-piperazine (1.45 g), to provide 4-[4-(3-cyclohexylpropyl)piperazin-1-yl]-2-fluorophenol hydrochloride (1.17 g).
$^1$H-NMR(CD$_3$OD, δ):0.95(2H, m), 1.1-1.4(6H, m), 1.6-1.9(7H, m), 3.19(2H, t, J=5.4 Hz), 3.36(2H, br s), 3.71(4H, br s), 6.8-7.1(3H, m). MS(m/z):320(M+-xHCl).

Production Example 52

4-[4-(3-Cyclohexylpropyl)piperazin-1-yl]-2-fluorophenol hydrochloride (1.45 g) was suspended in ethyl acetate, and to which saturated aqueous sodium hydrogencarbonate solution and 2 grains of sodium hydroxide were added by the order stated, to effect distribution. The ethyl acetate layer was washed with saturated saline solution, dried over anhydrous magnesium sulfate, and the solvent was distilled off. Purifying the resulting crude product on silica gel column chromatography (eluent, chloroform: methanol=10:1), 4-[4-(3-cyclohexylpropyl)piperazin-1-yl]-2-fluorophenol (910 mg) was obtained.

$^1$H-NMR(DMSO-d$_6$, δ):0.87(2H, m), 1.1-1.3(6H, m), 1.5-1.8(7H, m), 3.12(6H, br s), 3.56(2H, br s), 6.61(1H, d, J=8.9 Hz), 7.7-7.9(2H, m). MS(m/z):320(M$^+$).

Production Example 53

Production Example 9 was repeated except that 5-bromo-2-methoxytoluene and 1-(2-phenethyl)piperazine were replaced with 1-benzyloxy-4-bromo-2-fluorobenzene (6.742 g) and piperazine (12.404 g), respectively. The resulting crude product was purified on silica gel column chromatography (eluent, chloroform: methanol=2:1) to provide 1-(4-benzyloxy-3-fluorophenyl)piperazine (3.716 g).

$^1$H-NMR(CDCl$_3$, δ):2.93-3.17(8H, m), 5.08(2H, s), 6.58(1H, dd, J=2.7, 8.9 Hz), 6.72(1H, dd, J=2.9, 14.1 Hz), 6.92(1H, t, J=9.2 Hz), 7.27-7.48(5H, m). MS(m/z):286(M$^+$).

Production Example 54

Example 38 was repeated except that n-octyl bromide was replaced with 3-phenylpropyl bromide (151 μL), to provide crude 1-(4-benzyloxy-3-fluorophenyl)-4-(3-phenylpropyl) piperazine (401 mg).

$^1$H-NMR(CDCl$_3$, δ):1.78-1.90(2H, m), 2.41(2H, t, J=7.5 Hz), 2.52-2.61(4H, m), 2.64(2H, t, J=7.7 Hz), 3.05-3.15(4H, m), 5.05(2H, s), 6.55(1H, dd, J=2.7, 9.1 Hz), 6.70(1H, dd, J=2.7, 13.8 Hz), 6.89(1H, t, J=9.1 Hz), 7.12-7.47(10H, m). MS(m/z):404(M$^+$).

Production Example 55

Production Example 30 was repeated except that 1-(4-benzyloxy-3-chlorophenyl)-4-(3-cyclohexylpropyl)piperazine was replaced with 1-(4-benzyloxy-3-fluorophenyl)-4-(3-phenylpropyl)-piperazine (394 mg). The resulting crude product was purified on TLC (developer, chloroform: methanol=10:1) to provide 2-fluoro-4-[4-(3-phenylpropyl)piperazin-1-yl]phenol (224 mg).

$^1$H-NMR(CDCl$_3$, δ):1.78-1.92(2H, m), 2.33-2.48(2H, m), 2.53-2.62(4H, m), 2.60-2.73(2H, m), 3.05-3.13(4H, m), 6.56-6.62(1H, m), 6.68(1H, dd, J=2.9, 13.3 Hz), 6.88(1H, dd, J=8.9, 10.0 Hz), 7.13-7.35(5H, m). MS(m/z):314(M$^+$).

Production Example 56

Production Example 38 was repeated except that octyl bromide was replaced with 4-chloro-1-(4-tert-butylphenyl)-1-butanone (239 mg), to provide crude 4-[4-(4-benzyloxy-3-fluorophenyl)-piperazin-1-yl]-1-(4-tert-butylphenyl)-1-butanone (285 mg).

$^1$H-NMR(CDCl$_3$, δ):1.34(9H, s), 1.59(2H, br s), 1.97(2H, m), 2.4-3.1(10H, m), 5.06(2H, s), 6.54(1H, td, J=1.5, 8.9 Hz), 6.68(1H, dd, J=2.7, 13.8 Hz), 6.89(1H, t, J=8.9 Hz), 7.15-7.50(7H, m), 7.91(2H, d, J=8.5 Hz). MS(m/z):488(M$^+$).

Production Example 57

Production Example 30 was repeated except that 1-(4-benzyloxy-3-chlorophenyl)-4-(3-cyclohexylpropyl)piperazine was replaced with 4-[4-(4-benzyloxy-3-fluorophenyl) piperazin-1-yl]-1-(4-tert-butylphenyl)-1-butanone (274 mg), to provide 1-(4-tert-butylphenyl)-4-[4-(3-fluoro-4-hydroxyphenyl)piperazin-1-yl]-1-butanone hydrochloride (191 mg).

MS(m/z):398(M$^+$-xHCl).

Production Example 58

Production Example 3 was repeated except that 1-(4-methoxyphenyl)-piperazine dihydrochloride and isovaleryl chloride were replaced with 1-(4-benzyloxy-3-fluorophenyl)piperazine (286 mg) and valeryl chloride (131 μL), respectively, to provide crude 4-(4-benzyloxy-3-fluorophenyl)-1-valerylpiperazine (367 mg).

Production Example 59

Production Example 2 was repeated except that 1-(4-methoxyphenyl)-4-phenethylpiperazine was replaced with 4-(4-benzyloxy-3-fluorophenyl)-1-valerylpiperazine (367 mg). The resulting crude product was purified on TLC (developer, chloroform: methanol=12:1) to provide 4-(3-fluoro-4-hydroxyphenyl)-1-valerylpiperazine (61 mg).

Production Example 60

Production Example 30 was repeated except that 1-(4-benzyloxy-3-chlorophenyl)-4-(3-cyclohexylpropyl)piperazine was replaced with 1-(4-benzyloxy-3-fluorophenyl)piperazine (300 mg), to provide 2-fluoro-4-(piperazin-1-yl) phenol hydrochloride (267 mg).

$^1$H-NMR(DMSO-d$_6$, δ):6.5-7.1(3H, m). MS(m/z): 196 (M$^+$-xHCl).

Production Example 61

Production Example 3 was repeated except that 1-(4-methoxyphenyl)-piperazine dihydrochloride and isovaleryl chloride were replaced with 1-(4-benzyloxy-3-fluorophenyl)piperazine (286 mg) and diethylcarbamoyl chloride (139 μL), respectively, to provide crude N,N-diethyl-4-(4-benzyloxy-3-fluorophenyl)-1-piperazinecarboxamide (370 mg).

$^1$H-NMR(CDCl$_3$, δ):1.12(6H, t, J=7.1 Hz), 3.00-3.13(4H, m), 3.23(4H, q, J=7.3 Hz), 3.26-3.42(4H, m), 5.07(2H, s), 6.56(1H, dd, J=2.7, 8.9 Hz), 6.71(1H, dd, J=2.7, 13.9 Hz), 6.89(1H, t, J=9.3 Hz), 7.27-7.47(5H, m). MS(m/z):385(M$^+$).

Production Example 62

Production Example 30 was repeated except that 1-(4-benzyloxy-3-chlorophenyl)-4-(3-cyclohexylpropyl)piperazine was replaced with N,N-diethyl-4-(4-benzyloxy-3-fluorophenyl)-1-piperazinecarboxamide (365 mg). The resulting crude product was purified on TLC (developer, chloroform: methanol=12:1) to provide N,N-diethyl-4-(3-fluoro-4-hydroxyphenyl)-1-piperazinecarboxamide (160 mg).

Production Example 63

Production Example 26 was repeated except that 3-chloro-4-methoxymethoxyaniline was replaced with 2-fluoro-p-anisidine (1.123 g), to provide crude 1-(2-fluoro-4-methoxyphenyl)-piperazine (1.734 g).

Production Example 64

Production Example 1 was repeated except that 1-(4-methoxyphenyl)piperazine dihydrochloride was replaced with 1-(2-fluoro-4-methoxyphenyl)piperazine (1 g). The resulting crude product was purified on silica gel column chromatography (eluent, chloroform: acetone=6:1) to provide 1-(2-fluoro-4-methoxyphenyl)-4-phenethylpiperazine (374 mg).

$^1$H-NMR(CDCl$_3$, δ):2.60-2.78(6H, m), 2.78-2.87(2H, m), 3.00-3.10(4H, m), 3.72(3H, s), 6.58-6.68(2H, m), 6.90(1H, t, J=8.9 Hz), 7.13-7.32(5H, m). MS(m/z):314(M$^+$).

Production Example 65

Production Example 10 was repeated except that 1-(4-methoxy-3-methylphenyl)-4-phenethylpiperazine was replaced with 1-(2-fluoro-4-methoxyphenyl)-4-phenethylpiperazine (367 mg), and the resulting crude product was purified on TLC (developer, chloroform: methanol=17:1) to provide 3-fluoro-4-(4-phenethyl-piperazin-1-yl)phenol (178 mg).

$^1$H-NMR(CDCl$_3$, δ):2.63-2.80(6H, m), 2.80-2.90(2H, m), 3.00-3.16(4H, m), 6.52(1H, dd, J=2.7, 8.5 Hz), 6.58(1H, dd, J=2.7, 13.1 Hz), 6.85(1H, dd, J=8.9, 9.6 Hz), 7.17-7.36(5H, m). MS(m/z):300(M$^+$).

Production Example 66

Production Example 9 was repeated except that 5-bromo-2-methoxytoluene was replaced with 4-bromo-2,5-difluoroanisole (446 mg), and 1-phenethylpiperazine was replaced with 4-benzylpiperidine (2.30 mL). The resulting crude product was purified on silica gel column chromatography (eluent, hexane: ethyl acetate=4:1) to provide 4-benzyl-1-(2,5-difluoro-4-methoxyphenyl)piperidine (304 mg).

$^1$H-NMR(CDCl$_3$, δ):1.4-1.8(5H, m), 2.53(2H, dt, J=1.9, 11.6 Hz), 2.59(2H, d, J=6.9 Hz), 3.29(2H, br d, J=11.6 Hz), 3.82(3H, s), 6.65-6.80(2H, m), 7.1-7.3(5H, m). MS(m/z):317 (M$^+$).

Production Example 67

Production Example 2 was repeated except that 1-(4-methoxyphenyl)-4-phenethylpiperazine was replaced with 4-benzyl-1-(2,5-difluoro-4-methoxyphenyl)piperidine (300 mg). The resulting crude product was purified on silica gel column chromatography (eluent, hexane: ethyl acetate=4:1) to provide 4-(4-benzylpiperidino)-2,5-difluorophenol (138 mg).

MS(m/z):303(M$^+$).

Production Example 68

Production Example 9 was repeated except that 5-bromo-2-methoxytoluene and 1-phenethylpiperazine were replaced with 4-bromo-2,5-difluoroanisole (338 mg) and 4-(3-cyclohexylpropyl)-piperidine (953 mg), respectively. The resulting crude product was purified on silica gel column chromatography (eluent, hexane: ethyl acetate=3:1) to provide 4-(3-cyclohexylpropyl)-1-(2,5-difluoro-4-methoxyphenyl)piperidine (523 mg).

$^1$H-NMR(CDCl$_3$, δ):0.8-0.9(2H, m), 1.1-1.4(14H, m), 1.6-1.8(6H, m), 2.55(2H, t, J=11 Hz), 3.29(2H, d, J=12 Hz), 3.82(3H, s), 6.70(1H, dd, J=8, 13 Hz), 6.74(1H, dd, J=8, 13 Hz). MS(m/z):351(M$^+$), 336.

Production Example 69

Production Example 2 was repeated except that 1-(4-methoxyphenyl)-4-phenethylpiperazine was replaced with 4-(3-cyclohexylpropyl)-1-(2,5-difluoro-4-methoxyphenyl)piperidine (246 mg), to provide crude 4-[4-(3-cyclohexylpropyl)piperidino]-2,5-difluorophenol (599 mg).

Production Example 70

Production Example 9 was repeated except that 5-bromo-2-methoxytoluene and 1-(2-phenethyl)piperazine were replaced with 4-bromo-2,5-difluoroanisole (446 mg) and 4-(3-phenylpropyl)-piperidine (1.220 g), respectively. The resulting crude product was purified on silica gel column chromatography (eluent, hexane: ethyl acetate=8:1) to provide 1-(2,5-difluoro-4-methoxyphenyl)-4-(3-phenylpropyl) piperidine (233 mg).

$^1$H-NMR(CDCl$_3$, δ):1.30-1.48(5H, m), 1.62-1.72(2H, m), 1.78(2H, d, J=10.0 Hz), 2.55(2H, t, J=11.4 Hz), 2.60(2H, t, J=7.7 Hz), 3.30(2H, d, J=12.0 Hz), 3.82(3H, s), 6.65-6.80 (2H, m), 7.13-7.33(5H, m). MS(m/z):345(M$^+$).

Production Example 71

Production Example 10 was repeated except that 1-(4-methoxy-3-methylphenyl)-4-phenethylpiperazine was replaced with 1-(2,5-difluoro-4-methoxyphenyl)-4-(3-phenylpropyl)piperidine (230 mg). The resulting crude product was purified on TLC (developer, hexane: ethyl acetate=3:1) to provide 2,5-difluoro-4-[4-(3-phenylpropyl)piperidino]phenol (71 mg).

$^1$H-NMR(CDCl$_3$, δ):1.28-1.48(5H, m), 1.61-1.72(2H, m), 1.77(2H, d, J=10.0 Hz), 2.53(2H, t, J=11.2 Hz), 2.60(2H, t, J=7.7 Hz), 3.28(2H, d, J=11.9 Hz), 6.67-6.78(2H, m), 7.12-7.33(5H, m). MS(m/z):331(M$^+$).

Production Example 72

Production Example 9 was repeated except that 5-bromo-2-methoxytoluene and 1-phenethylpiperazine were replaced with 4-bromo-2,5-difluoroanisole (1.115 g) and 1,4-dioxa-8-azaspiro[4,5]-decane (859 mg), respectively. The resulting crude product was purified on silica gel column chromatography (eluent, hexane: ethyl acetate=3:1) to provide 8-(2,5-difluoro-4-methoxyphenyl)-1,4-dioxa-8-azaspiro[4,5]decane (455 mg).

$^1$H-NMR(CDCl$_3$, δ):1.87(4H, t, J=6 Hz), 3.07(4H, t, J=6 Hz), 3.82(3H, s), 3.98(4H, s), 6.71(1H, dd, J=8, 13 Hz), 6.76(1H, dd, J=8, 13 Hz). MS(m/z):285(M$^+$), 270, 240.

Production Example 73

A mixture of 8-(2,5-difluoro-4-methoxyphenyl)-1,4-dioxa-8-azaspiro[4,5]decane (8 g), p-toluenesulfonic acid monohydrate (11.8 g), acetone (1.4 L) and water (140 mL) was refluxed for 5 hours. After allowing the reaction mixture to cool off, saturated aqueous sodium hydrogencarbonate solution was added thereto and the system was extracted with ethyl acetate. The organic layer was washed with saturated saline solution and dried over anhydrous sodium sulfate. Distilling the solvent off, 1-(2,5-difluoro-4-methoxyphenyl)piperidin-4-one (6.967 g) was obtained.

$^1$H-NMR(CDCl$_3$, δ):2.60(4H, t, J=6 Hz), 3.30(4H, t, J=6 Hz), 3.84(3H, s), 6.75(1H, dd, J=8, 13 Hz), 6.78(1H, dd, J=8, 12 Hz). MS(m/z):241(M$^+$), 226, 198.

Production Example 74

A reaction vessel was charged with methoxymethyltriphenyl-phosphonium chloride (1.114 g), the atomosphere indide the vessel was substituted with nitrogen, and anhydrous tetrahydrofuran (2 mL) was added, followed by further dropwise addition of 1.57 M n-butyl lithium-in-hexane solution (2 mL) at room temperature and thereafter 10 minutes' stirring at room temperature. To the reaction mixture a mixture of 1-(2,5-difluoro-4-methoxyphenyl)piperidin-4-one (676 mg) and anhydrous tetrahydrofuran (0.5 mL) was added dropwise, followed by 30 minutes' stirring at room temperature. To the reaction mixture water was added, followed by extraction with ethyl acetate. The organic layer was washed with saturated saline solution and dried over anhydrous sodium sulfate. Distilling the solvent off, the crude product as obtained was purified on silica gel column chromatography (eluent, hexane: ethyl acetate=10:1) to provide 1-(2,5-difluoro-4-methoxyphenyl)-4-methoxymethylenepiperidine (257 mg).

$^1$H-NMR(CDCl$_3$, δ):2.18-2.23(2H, m), 2.42-2.47(2H, m), 2.89-2.95(4H, m), 3.56(3H, s), 3.82(3H, s), 5.85(1H, br s), 6.67-6.76(2H, m). MS(m/z):269(M$^+$), 254.

Production, Example 75

A mixture of 1-(2,5-difluoro-4-methoxyphenyl)-4-methoxy-methylenepiperidine (89 mg), tetrahydrofuran (1.58 mL) and conc. hydrochloric acid (0.12 mL) was stirred for 2 hours at room temperature. After adding saturated aqueous sodium hydrogencarbonate solution to the reaction mixture, the product was extracted with ethyl acetate. The organic layer was washed with water and dried over anhydrous sodium sulfate. Distilling the solvent off, 1-(2,5-difluoro-4-methoxyphenyl)-4-piperidinecarbaldehyde (86 mg) was obtained.

$^1$H-NMR(CDCl$_3$, δ):1.8-1.9(2H, m), 1.98-2.06(2H, m), 2.3-2.4(1H, m), 2.69-2.77(2H, m), 3.24-3.30(2H, m), 3.82(3H, s), 6.68-6.77(2H, m), 9.70(1H, d, J=1 Hz). MS(m/z):255(M$^+$), 240.

Production Example 76

Production Example 74 was repeated except that methoxymethyltriphenylphosphonium chloride and 1-(2,5-difluoro-4-methoxyphenyl)piperidin-4-one were replaced with phenethyltri-phenylphosphonium bromide (133 mg) and 1-(2,5-difluoro-4-methoxyphenyl)-4-piperidinecarbaldehyde (35 mg), respectively, and the resulting crude product was purified on TLC (developer, hexane: ethyl acetate=10:1) to provide (Z)-1-(2,5-difluoro-4-methoxyphenyl)-4-(3-phenyl-1-propen-1-yl)piperidine (37 mg).

$^1$H-NMR(CDCl$_3$, δ):1.6-1.8(4H, m), 2.46-2.59(1H, m), 2.6-2.7(2H, m), 3.28-3.36(2H, m), 3.44(2H, d, J=7 Hz), 3.82(3H, s), 5.39-5.46(1H, m), 5.51-5.60(1H, m), 6.71(1H, dd, J=8, 13 Hz), 6.76(1H, dd, J=8, 13 Hz), 7.16-7.22(3H, m), 7.26-7.32(2H, m). MS(m/z):343(M$^+$), 224.

Production Example 77

Production Example 2 was repeated except that 1-(4-methoxyphenyl)-4-phenethylpiperazine was replaced with (Z)-1-(2,5-difluoro-4-methoxyphenyl)-4-(3-phenyl-1-propen-1-yl)piperidine (18 mg), to provide crude (Z)-2,5-difluoro-4-[4-(3-phenyl-1-propen-1-yl)-piperidino]phenol (48 mg).

Production Example 78

Production Example 9 was repeated except that 5-bromo-2-methoxytoluene and 1-(2-phenethyl)piperazine were replaced with 4-bromo-2,5-difluoroanisole (4.460 g) and ethyl isonipecotate (3.70 mL), respectively. The resulting crude product was purified on silica gel column chromatography (eluent, hexane: ethyl acetate=6:1) to provide ethyl 1-(2,5-difluoro-4-methoxyphenyl)piperidine-4-carboxylate (2.465 g).

$^1$H-NMR(CDCl$_3$, δ):1.28(3H, t, J=7.1 Hz), 1.87-2.08(4H, m), 2.34-2.47(1H, m), 2.69(2H, dt, J=2.7, 11.4 Hz), 3.25-3.34(2H, m), 3.82(3H, s), 4.18(2H, q, J=7.3 Hz), 6.68-6.81(2H, m). MS(m/z):299(M$^+$).

Production Example 79

A mixture of ethyl 1-(2,5-difluoro-4-methoxyphenyl)piperidine-4-carboxylate (1.196 g), potassium hydroxide (782 mg), ethanol (11 mL) and water (0.6 mL) was heated under reflux for 1.5 hours. The reaction liquid was rendered acidic with diluted hydrochloric acid under cooling with ice, and the product was extracted with ethyl acetate. The organic layer was washed with saturated saline solution and dried over anhydrous magnesium sulfate. Distilling the solvent off, crude 1-(2,5-difluoro-4-methoxyphenyl)piperidine-4-carboxylic acid (1.036 g) was obtained.

$^1$H-NMR(DMSO-d$_6$, δ):1.62-1.77(2H, m), 1.91(2H, dd, J=3.3, 13.3 Hz), 2.30-2.40(1H, m), 2.68(2H, t, J=11.6 Hz), 3.13-3.24(2H, m), 3.80(3H, s), 6.95(1H, dd, J=8.5, 13.1 Hz), 7.10(1H, dd, J=8.1, 13.5 Hz), 12.20(1H, s). MS(m/z):271 (M$^+$).

Production Example 80

A mixture of 1-(2,5-difluoro-4-methoxyphenyl)piperidine-4-carboxylic acid (170 mg), toluene (3.5 mL), pyridine (76 μL), one drop of N,N-dimethylformamide and thionyl chloride (69 μL) was stirred for an hour at room temperature. After distilling the solvent off, pyridine (1.9 mL) and 1-ethylpropylamine (197 μL) were added to the remaining product under cooling with ice. Raising the temperature to the ambient level, the system was stirred for 3.5 hours. The reaction mixture was poured in saturated saline solution, and the resulting product was extracted with ethyl acetate. The organic layer was washed with saturated saline solution and dried over anhydrous magnesium sulfate. Distilling the solvent off, crude 1-(2,5-difluoro-4-methoxyphenyl)-N-(1-ethylpropyl)-4-piperidine-carboxamide (167 mg) was obtained.

Production Example 81

Production Example 2 was repeated except that 1-(4-methoxyphenyl)-4-phenethylpiperazine was replaced with 1-(2,5-difluoro-4-methoxyphenyl)-N-(1-ethylpropyl)-4-piperidine-carboxamide (167 mg). The resulting crude product was purified on TLC (developer, chloroform: methanol=12:1) to provide 1-(2,5-difluoro-4-hydroxyphenyl)-N-(1-ethylpropyl)-4-piperidinecarboxamide (95 mg).

$^1$H-NMR(DMSO-d$_6$, δ):0.80(6H, t, J=7.3 Hz), 1.22-1.37(2H, m), 1.37-1.50(2H, m), 1.65-1.81(4H, m), 2.15-2.28(1H, m), 2.50-2.63(2H, m), 3.20(2H, d, J=11.6 Hz), 3.48-3.60(1H, m), 6.72(1H, dd, J=8.1, 13.1 Hz), 6.88(1H, dd, J=8.1, 12.7 Hz), 7.41(1H, d, J=8.9 Hz), 9.70(1H, s). MS(m/z):326(M$^+$).

Production Example 82

Production Example 80 was repeated except that 1-ethylpropylamine was replaced with piperidine (384 μL), to provide crude 1-[1-(2,5-difluoro-4-methoxyphenyl)-4-piperidylcarbonyl]-piperidine (407 mg).

Production Example 83

Production Example 2 was repeated except that 1-(4-methoxyphenyl)-4-phenethylpiperazine was replaced with 1-[1-(2,5-difluoro-4-methoxyphenyl)-4-piperidylcarbonyl]piperidine (406 mg). The resulting crude product was purified on TLC (developer, chloroform: methanol=12:1) to provide 1-[1-(2,5-difluoro-4-hydroxyphenyl)-4-piperidylcarbonyl] piperidine (178 mg).
$^1$H-NMR(DMSO-$d_6$, δ):1.35-1.79(10H, m), 2.67-2.80 (3H, m), 3.20(2H, d, J=12.7 Hz), 3.23-3.52(4H, m), 6.72(1H, dd, J=8.1, 13.1 Hz), 6.85(1H, dd, J=8.3, 12.9 Hz), 9.69(1H, s). MS(m/z):324(M$^+$).

Production Example 84

Production Example 1 was repeated except that 1-(4-methoxyphenyl)piperazine dihydrochloride and (2-bromoethyl)-benzene were replaced with 1-(2,5-difluoro-4-methoxyphenyl)-piperazine (114 mg) and 1-bromodecane (114 μL), respectively, to provide crude 1-decyl-4-(2,5-difluoro-4-methoxyphenyl)piperazine (179 mg).
$^1$H-NMR(CDCl$_3$, δ):0.88(3H, t, J=6.8 Hz), 1.13-1.73 (16H, m), 2.40(2H, t, J=7.7 Hz), 2.60(4H, br s), 2.93-3.12 (4H, m), 3.82(3H, s), 6.67-6.82(2H, m). MS(m/z):368(M$^+$).

Production Example 85

Production Example 10 was repeated except that 1-(4-methoxy-3-methylphenyl)-4-phenethylpiperazine was replaced with 1-decyl-4-(2,5-difluoro-4-methoxyphenyl) piperazine (176 mg). The resulting crude product was purified on TLC (developer, chloroform: methanol=19:1) to provide 4-(4-decylpiperazin-1-yl)-2,5-difluorophenol (67 mg).
$^1$H-NMR(DMSO-$d_6$, δ):0.84(3H, t, J=6.8 Hz), 1.15-1.32 (14H, m), 1.33-1.49(2H, m), 2.28(2H, t, J=7.3 Hz), 2.46(4H, br s), 2.80-2.90(4H, m), 6.71(1H, dd, J=8.1, 13.1 Hz), 6.85 (1H, dd, J=8.3, 12.9 Hz). MS(m/z):354 (M$^+$).

Production Example 86

Production Example 1 was repeated except that 1-(4-methoxyphenyl)piperazine dihydrochloride and (2-bromoethyl)-benzene were replaced with 1-(2,5-difluoro-4-methoxyphenyl)-piperazine (342 mg) and 2-cyclohexylethyl methylsulfonate (309 mg), respectively, to provide crude 1-(2-cyclohexylethyl)-4-(2,5-difluoro-4-methoxyphenyl) piperazine (476 mg).

Production Example 87

Production Example 10 was repeated except that 1-(4-methoxy-3-methylphenyl)-4-phenethylpiperazine was replaced with 1-(2-cyclohexylethyl)-4-(2,5-difluoro-4-methoxyphenyl)-piperazine (250 mg). The resulting crude product was purified on TLC (developer, chloroform: methanol=13: 1) to provide 4-[4-(2-cyclohexylethyl)piperazin-1-yl]-2,5-difluorophenol (87 mg).
$^1$H-NMR(DMSO-$d_6$, δ):0.82-0.97(2H, m), 1.06-1.39(6H, m), 1.56-1.74(5H, m), 2.32(2H, t, J=7.1 Hz), 2.47(4H, br s), 2.80-2.93(4H, m), 6.72(1H, dd, J=8.1, 13.1 Hz), 6.87(1H, dd, J=8.3, 12.9 Hz), 9.70(1H, s). MS(m/z):324(M$^+$).

Production Example 88

Production Example 9 was repeated except that 5-bromo-2-methoxytoluene was replaced with 4-bromo-2,5-difluoroanisole (446 mg). The resulting crude product was purified on silica gel column chromatography (eluent, chloroform: acetone=12:1) to provide 1-(2,5-difluoro-4-methoxyphenyl)-4-phenethylpiperazine (576 mg).
$^1$H-NMR(CDCl$_3$, δ):2.60-2.78(6H, m), 2.78-2.90(2H, m), 2.98-3.12(4H, m), 3.82(3H, s), 6.68-6.82(2H, m), 7.17-7.35 (5H, m). MS(m/z):332(M$^+$).

Production Example 89

Production Example 10 was repeated except that 1-(4-methoxy-3-methylphenyl)-4-phenethylpiperazine was replaced with 1-(2,5-difluoro-4-methoxyphenyl)-4-phenethylpiperazine (571 mg). The resulting crude product was purified on TLC (developer, chloroform: methanol=15:1) to provide 2,5-difluoro-4-(4-phenethylpiperazin-1-yl)phenol (470 mg).
$^1$H-NMR(CDCl$_3$, δ):2.60-2.79(6H, m), 2.79-2.90(2H, m), 2.93-3.16(4H, m), 6.66-6.80(2H, m), 7.16-7.38(5H, m). MS(m/z):318(M$^+$).

Production Example 90

Production Example 1 was repeated except that 1-(4-methoxyphenyl)piperazine dihydrochloride and (2-bromoethyl)-benzene were replaced with 1-(2,5-difluoro-4-methoxyphenyl)-piperazine (342 mg) and 3-cyclopentylpropyl methylsulfonate (309 mg), respectively, to provide crude 1-(3-cyclopentylpropyl)-4-(2,5-difluoro-4-methoxyphenyl) piperazine (486 mg).

Production Example 91

Production Example 10 was repeated except that 1-(4-methoxy-3-methylphenyl)-4-phenethylpiperazine was replaced with 1-(3-cyclopentylpropyl)-4-(2,5-difluoro-4-methoxyphenyl)-piperazine (250 mg). The resulting crude product was purified on TLC (developer, chloroform: methanol=16:1) to provide 4-[4-(3-cyclopentylpropyl)piperazin-1-yl]-2,5-difluorophenol (83 mg).
$^1$H-NMR(DMSO-$d_6$, δ):0.97-1.13(2H, m), 1.22-1.32(2H, m), 1.39-1.66(6H, m), 1.67-1.81(3H, m), 2.29(2H, t, J=7.3 Hz), 2.48(4H, br s), 2.82-2.91(4H, m), 6.72(1H, dd, J=8.5, 13.1 Hz), 6.86(1H, dd, J=8.5, 12.7 Hz), 9.70(1H, 5). MS(m/z):324(M$^+$).

Production Example 92

Production Example 38 was repeated except that 1-(4-benzyloxy-3-fluorophenyl)piperazine and n-octyl bromide were replaced with 1-(2,5-difluoro-4-methoxyphenyl)piperazine (228 mg) and 3-cyclohexylpropyl chloride (161 mg). The resulting crude product was purified on silica gel column chromatography (eluent, ethyl acetate) to provide 1-(3-cyclohexylpropyl)-4-(2,5-difluoro-4-methoxyphenyl)piperazine (342 mg).
$^1$H-NMR(CDCl$_3$, δ):0.8-1.8(15H, m), 2.32-2.38(2H, m), 2.57-2.64(4H, m), 2.95-3.05(4H, m), 3.82(3H, s), 6.67-7.67 (2H, m). MS(m/z):352(M$^+$), 241.

Production Example 93

Production Example 38 was repeated except that 1-(4-benzyloxy-3-fluorophenyl)piperazine and n-octyl bromide were replaced with 1-(2,5-difluoro-4-methoxyphenyl)piperazine (5.72 g) and 3-cyclohexylpropyl methanesulfonate (5.52 g), to provide crude 1-(3-cyclohexylpropyl)-4-(2,5-difluoro-4-methoxyphenyl)piperazine (8.618 g).

Production Example 94 p-Toluenesulfonic acid monohydrate (1.042 g), 48% hydrobromic acid (0.62 mL), pyridine (0.89 mL) and toluene (5 mL) were mixed, and the solvent was distilled off under ambient pressure. To the residue 1-(3-cyclohexylpropyl)-4-(2,5-difluoro-4-methoxyphenyl)piperazine (322 mg) and toluene (5 mL) were added, and the solvent was distilled off under ambient pressure. The residue was stirred for 2 hours on an oil bath of 200° C., and the reaction mixture was let stand to cool off, followed by addition of saturated aqueous sodium hydrogencarbonate solution and extraction with ethyl acetate. The organic layer was washed with saturated saline solution and dried over anhydrous sodium sulfate. Distilling the solvent off, the resulting crude product was purified on TLC (developer, ethyl acetate: hexane=1:1) to provide 4-[4-(3-cyclo-hexylpropyl)piperazin-1-yl]-2,5-difluorophenol (134 mg).

$^1$H-NMR(DMSO-d$_6$, δ):0.8-0.9(2H, m), 1.1-1.2(6H, m), 1.37-1.47(2H, m), 1.55-1.70(5H, m), 2.25(2H, br t, J=7 Hz), 2.42-2.48(4H, m), 2.85(4H, br t, J=5 Hz), 6.71(1H, dd, J=8, 13 Hz), 6.84(1H, dd, J=8, 13 Hz), 9.68(1H, s). MS(m/z):338 (M$^+$), 227.

Production Example 95

Production Example 1 was repeated except that 1-(4-methoxyphenyl)piperazine dihydrochloride and (2-bromoethyl)benzene were replaced with 1-(2,5-difluoro-4-methoxyphenyl)-piperazine (342 mg) and 4-cyclohexylbutyl methylsulfonate (351 mg), respectively, to provide crude 1-(4-cyclohexylbutyl)-4-(2,5-difluoro-4-methoxyphenyl)piperazine (532 mg).

Production Example 96

Production Example 10 was repeated except that 1-(4-methoxy-3-methylphenyl)-4-phenethylpiperazine was replaced with 1-(4-cyclohexylbutyl)-4-(2,5-difluoro-4-methoxyphenyl)-piperazine (482 mg). The resulting crude product was purified on TLC (developer, chloroform: methanol=16:1) to provide 4-[4-(4-cyclohexylbutyl)piperazin-1-yl]-2,5-difluorophenol (128 mg).

$^1$H-NMR(DMSO-d$_6$, δ):0.78-0.92(2H, m), 1.08-1.33(8H, m), 1.35-1.47(2H, m), 1.56-1.72(5H, m), 2.29(2H, t, J=7.3 Hz), 2.47(4H, br s), 2.82-2.92(4H, m), 6.72(1H, dd, J=8.1, 13.1 Hz), 6.86(1H, dd, J=8.5, 12.7 Hz), 9.70(1H, s). MS(m/z):352(M$^+$).

Production Example 97

Production Example 38 was repeated except that 1-(4-benzyloxy-3-fluorophenyl)piperazine and n-octyl bromide were replaced with 1-(2,5-difluoro-4-methoxyphenyl)piperazine (228 mg) and 3-chloro-1-phenylpropan-1-one (169 mg), to provide crude 3-[4-(2,5-difluoro-4-methoxyphenyl)piperazin-1-yl]-1-phenylpropan-1-one (365 mg).

$^1$H-NMR(CDCl$_3$, δ):2.68(4H, br t, J=5 Hz), 2.90(2H, t, J=7 Hz), 3.01(4H, br t, J=5 Hz), 3.21(2H, t, J=7 Hz), 3.82(3H, s), 6.68-6.77(2H, m), 7.44-7.49(2H, m), 7.54-7.59(1H, m), 7.95-7.98(2H, m). MS(m/z):360(M$^+$), 345, 241.

Production Example 98

Production Example 2 was repeated except that 1-(4-methoxyphenyl)-4-phenethylpiperazine was replaced with 3-[4-(2,5-difluoro-4-methoxyphenyl)piperazin-1-yl]-1-phenylpropan-1-one (344 mg), to provide crude 3-[4-(2,5-difluoro-4-hydroxyphenyl)-piperazin-1-yl]-1-phenylpropan-1-one (334 mg).

Production Example 99

Production Example 38 was repeated except that 1-(4-benzyloxy-3-fluorophenyl)piperazine and n-octyl bromide were replaced with 1-(2,5-difluoro-4-methoxyphenyl)piperazine (228 mg) and 1-(4-tert-butylphenyl)-4-chlorobutan-1-one (239 mg). The resulting crude product was purified on silica gel column chromatography (eluent, ethyl acetate) to provide 1-(4-tert-butylphenyl)-4-[4-(2,5-difluoro-4-methoxyphenyl)piperazin-1-yl]-butan-1-one (343 mg).

$^1$H-NMR(CDCl$_3$, δ):1.33(9H, s), 1.9-2.0(2H, m), 2.47(2H, t, J=7 Hz), 2.60(4H, br t, J=5 Hz), 2.95(4H, br t, J=5 Hz), 2.99(2H, t, J=7 Hz), 3.82(3H, s), 6.67-6.74(2H, m), 7.46(2H, d, J=7 Hz), 7.91(2H, d, J=8 Hz). MS(m/z):430(M$^+$), 415, 254.

Production Example 100

Production Example 94 was repeated except that 1-(3-cyclohexylpropyl)-4-(2,5-difluoro-4-methoxyphenyl)piperazine was replaced with 1-(4-tert-butylphenyl)-4-[4-(2,5-difluoro-4-methoxyphenyl)piperazin-1-yl]butan-1-one (330 mg). The resulting crude product was purified on TLC (developer, ethyl acetate: hexane=2:1) to provide 1-(4-tert-butylphenyl)-4-[4-(2,5-difluoro-4-hydroxyphenyl)piperazin-1-yl]butan-1-one (146 mg).

$^1$H-NMR(DMSO-d$_6$, δ):1.29(9H, s), 1.76-1.84(2H, m), 2.35(2H, t, J=7 Hz), 2.4-2.5(4H, m), 2.7-2.8(4H, m), 2.98(2H, t, J=7 Hz), 6.70(1H, dd, J=8, 13 Hz), 6.78(1H, dd, J=8, 13 Hz), 7.52(2H, d, J=8 Hz), 7.89(2H, d, J=8 Hz), 9.68(1H, s). MS(m/z):416(M$^+$), 401, 240.

Production Example 101

Production Example 3 was repeated except that 1-(4-methoxyphenyl)piperazine dihydrochloride and isovaleryl chloride were replaced with 1-(2,5-difluoro-4-methoxyphenyl)-piperazine (228 mg) and decanoyl chloride (205 μL), respectively, to provide crude 1-decanoyl-4-(2,5-difluoro-4-methoxyphenyl)piperazine (371 mg).

Production Example 102

Production Example 2 was repeated except that 1-(4-methoxyphenyl)-4-phenethylpiperazine was replaced with 1-decanoyl-4-(2,5-difluoro-4-methoxyphenyl)piperazine (371 mg). The resulting crude product was purified on TLC (developer, chloroform: methanol=19:1) to provide 1-decanoyl-4-(2,5-difluoro-4-hydroxyphenyl)piperazine (268 mg).

$^1$H-NMR(DMSO-d$_6$, δ):0.85(3H, t, J=6.9 Hz), 1.26(12H, br s), 1.43-1.56(2H, m), 2.30(2H, t, J=7.5 Hz), 2.76-2.92(4H, m), 3.57(4H, br s), 6.74(1H, dd, J=8.1, 13.1 Hz), 6.89(1H, dd, J=8.5, 12.7 Hz), 9.79(1H, s). MS(m/z):368(M$^+$).

Production Example 103

Production Example 3 was repeated except that 1-(4-methoxyphenyl)piperazine dihydrochloride and isovaleryl chloride were replaced with 1-(2,5-difluoro-4-methoxyphenyl)piperazine (228 mg) and 4-tert-butylbenzoyl chloride (234 μL), respectively, to provide crude 1-(4-tert-butylbenzoyl)-4-(2,5-difluoro-4-methoxyphenyl)piperazine (433 mg).

Production Example 104

Production Example 2 was repeated except that 1-(4-methoxyphenyl)-4-phenethylpiperazine was replaced with 1-(4-tert-butylbenzoyl)-4-(2,5-difluoro-4-methoxyphenyl)piperazine (433 mg), to provide crude 1-(4-tert-butylbenzoyl)-4-(2,5-difluoro-4-hydroxyphenyl)piperazine (282 mg).

$^1$H-NMR(DMSO-d$_6$, δ):1.29(9H, s), 2.90(4H, br s), 3.40-3.90(4H, m), 6.74(1H, dd, J=8.3, 12.9 Hz), 6.91(1H, dd, J=8.1, 12.7 Hz), 7.35(2H, d, J=6.6 Hz), 7.48(2H, d, J=6.6 Hz), 9.80(1H, s). MS(m/z):374(M$^+$).

Production Example 105

Production Example 3 was repeated except that 1-(4-methoxyphenyl)piperazine dihydrochloride and isovaleryl chloride were replaced with 1-(2,5-difluoro-4-methoxyphenyl)piperazine (228 mg) and 3-phenylpropionyl chloride (178 μL), respectively, to provide crude 4-(2,5-difluoro-4-methoxyphenyl)-1-(3-phenylpropanoyl)piperazine (348 mg).

$^1$H-NMR(CDCl$_3$, δ):2.64(2H, t, J=7.9 Hz), 2.75-2.83(2H, m), 2.83-2.93(2H, m), 2.98(2H, t, J=7.9 Hz), 3.45-3.54(2H, m), 3.70-3.81(2H, m), 3.82(3H, s), 6.62-6.78(2H, m), 7.15-7.36(5H, m). MS(m/z):360(M$^+$).

Production Example 106

Production Example 2 was repeated except that 1-(4-methoxyphenyl)-4-phenethylpiperazine was replaced with 4-(2,5-difluoro-4-methoxyphenyl)-1-(3-phenylpropanoyl)piperazine (344 mg). The resulting crude product was purified on TLC (developer, chloroform: methanol=15:1) to provide 4-(2,5-difluoro-4-hydroxyphenyl)-1-(3-phenylpropanoyl)piperazine (247 mg).

$^1$H-NMR(CDCl$_3$, δ):2.67(2H, t, J=7.9 Hz), 2.72-2.83(2H, m), 2.83-2.92(2H, m), 3.00(2H, t, J=7.9 Hz), 3.43-3.62(2H, m), 3.67-3.86(2H, m), 5.64(1H, s), 6.66(1H, dd, J=7.7, 11.9 Hz), 6.76(1H, dd, J=8.1, 12.3 Hz), 7.12-7.42(5H, m). MS(m/z):346(M$^+$).

Production Example 107

Production Example 9 was repeated except that 5-bromo-2-methoxytoluene, 1-(2-phenethyl)piperazine and ethyl acetate (extraction solvent) were replaced with 4-bromo-2,5-difluoroanisole (6.742 g), piperazine (12.404 g) and toluene (extraction solvent), respectively, to provide crude 1-(2,5-difluoro-4-methoxyphenyl)-piperazine (1.926 g).

Production Example 108

Production Example 3 was repeated except that 1-(4-methoxyphenyl)piperazine dihydrochloride and isovaleryl chloride were replaced with 1-(2,5-difluoro-4-methoxyphenyl)-piperazine (456 mg) and 1-octanesulfonyl chloride (470 μL), respectively, to provide crude 4-(2,5-difluoro-4-methoxyphenyl)-1-(octylsulfonyl)piperazine (681 mg).

Production Example 109

Production Example 2 was repeated except that 1-(4-methoxyphenyl)-4-phenethylpiperazine was replaced with 4-(2,5-difluoro-4-methoxyphenyl)-1-(octylsulfonyl)piperazine (300 mg). The resulting crude product was purified on TLC (developer, hexane: ethyl acetate=11:5) to provide 4-(2,5-difluoro-4-hydroxyphenyl)-1-(octylsulfonyl)piperazine (253 mg).

$^1$H-NMR(CDCl$_3$, δ):0.88(3H, t, J=7.0 Hz), 1.21-1.38(8H, m), 1.38-1.50(2H, m), 1.78-1.90(2H, m), 2.88-3.10(6H, m), 3.39-3.50(4H, m), 6.69-6.82(2H, m). MS(m/z):390(M$^+$).

Production Example 110

Production Example 3 was repeated except that 1-(4-methoxyphenyl)piperazine dihydrochloride and isovaleryl chloride were replaced with 1-(2,5-difluoro-4-methoxyphenyl)-piperazine (170 mg) and 2-mesitylenesulfonyl chloride (196 mg), respectively, to provide crude 4-(2,5-difluoro-4-methoxyphenyl)-1-(1,3,5-trimethylphenylsulfonyl)piperazine (277 mg).

$^1$H-NMR(CDCl$_3$, δ):2.30(3H, s), 2.63(6H, s), 2.93-3.04 (4H, m), 3.27-3.36(4H, m), 3.82(3H, s), 6.66-6.77(2H, m), 6.97(2H, s). MS(m/z):410(M$^+$).

Production Example 111

Production Example 2 was repeated except that 1-(4-methoxyphenyl)-4-phenethylpiperazine was replaced with 4-(2,5-difluoro-4-methoxyphenyl)-1-(1,3,5-trimethylphenylsulfonyl)-piperazine (268 mg). The resulting crude product was purified on TLC (developer, hexane: ethyl acetate=2:1) to provide 4-(2,5-difluoro-4-hydroxyphenyl)-1-(1,3,5-trimethylphenylsulfonyl)-piperazine (135 mg).

$^1$H-NMR(CDCl$_3$, δ):2.31(3H, s), 2.63(6H, s), 2.96-3.02 (4H, m), 3.27-3.38(4H, m), 4.99(1H, d, J=3.1 Hz), 6.63-6.80 (2H, m), 6.97(2H, s). MS(m/z):396(M$^+$).

Production Example 112

Production Example 3 was repeated except that 1-(4-methoxyphenyl)piperazine dihydrochloride and isovaleryl chloride were replaced with 1-(2,5-difluoro-4-methoxyphenyl)-piperazine (456 mg) and 4-fluorobenzenesulfonyl chloride (467 mg), respectively, to provide crude 4-(2,5-difluoro-4-methoxyphenyl)-1-4-fluorophenylsulfonyl)piperazine (725 mg).

Production Example 113

Production Example 2 was repeated except that 1-(4-methoxyphenyl)-4-phenethylpiperazine was replaced with 4-(2,5-difluoro-4-methoxyphenyl)-1-(4-fluorophenylsulfonyl)-piperazine (300 mg). The resulting crude product was purified on TLC (developer, hexane: ethyl acetate=2:1) to provide 4-(2,5-difluoro-4-hydroxyphenyl)-1-(4-fluorophenylsulfonyl)-piperazine (211 mg).

$^1$H-NMR(CDCl$_3$, δ):3.02-3.12(4H, m), 3.14-3.25(4H, m), 5.06(1H, s), 6.66-6.80(2H, m), 7.19-7.30(2H, m), 7.75-7.87 (2H, m). MS(m/z):372(M$^+$).

Production Example 114

Production Example 3 was repeated except that 1-(4-methoxyphenyl)piperazine dihydrochloride and isovaleryl chloride were replaced with 1-(2,5-difluoro-4-methoxyphenyl)- piperazine (500 mg) and 4-chlorobenzenesulfonyl chloride (694 mg), respectively, to provide 1-(4-chlorobenzenesulfonyl)-4-(2,5-difluoro-4-methoxyphenyl)piperazine (811 mg).

$^1$H-NMR(CDCl$_3$, δ):3.00-3.25(8H, m), 3.82(3H, s), 6.71 (2H, m), 7.54, 7.72(4H, AB, J=8.9 Hz). MS(m/z):402(M$^+$).

Production Example 115

Production Example 2 was repeated except that 1-(4-methoxyphenyl)-4-phenethylpiperazine was replaced with 1-(4-chlorobenzenesulfonyl)-4-(2,5-difluoro-4-methoxyphenyl)-piperazine (395 mg). The resulting crude product was purified on silica gel column chromatography (eluent, hexane: ethyl acetate=2:1) to provide 1-(4-chlorophenylsulfonyl)-4-(2,5-difluorophenyl)-piperazine (322 mg).

$^1$H-NMR(CD$_3$OD, δ):2.9-3.2(8H, m), 6.63(1H, dd, J=8.1, 12.7 Hz), 6.81(1H, dd, J=8.1, 12.3 Hz), 7.66, 7.79(4H, AB, J=8.9 Hz). MS(m/z):388(M$^+$).

Production Example 116

Production Example 3 was repeated except that 1-(4-methoxyphenyl)piperazine dihydrochloride and isovaleryl chloride were replaced with 1-(2,5-difluoro-4-methoxyphenyl)-piperazine (228 mg) and 4-chlorobenzylsulfonyl chloride (338 mg), respectively, to provide crude 1-(4-chlorobenzylsulfonyl)-4-(2,5-difluoro-4-methoxyphenyl)piperazine (419 mg).

$^1$H-NMR(DMSO-d$_6$, δ):2.7-3.1(4H, m), 3.2-3.4(4H, m), 3.79(3H, s), 4.49(2H, s), 6.8-7.3(2H, m), 7.4-7.6(4H, m). MS(m/z):416(M$^+$), 382, 366, 227.

Production Example 117

Production Example 2 was repeated except that 1-(4-methoxyphenyl)-4-phenethylpiperazine was replaced with 1-(4-chlorobenzylsulfonyl)-4-(2,5-difluoro-4-methoxyphenyl)-piperazine (400 mg), to provide crude 1-(4-chlorobenzylsulfonyl)-4-(2,5-difluoro-4-hydroxyphenyl) piperazine (380 mg).

Production Example 118

Production Example 3 was repeated except that 1-(4-methoxyphenyl)piperazine dihydrochloride and isovaleryl chloride were replaced with 1-(2,5-difluoro-4-methoxyphenyl)-piperazine (228 mg) and phenethylsulfonyl chloride (409 mg), respectively, to provide crude 4-(2,5-difluoro-4-methoxyphenyl)-1-phenethylsulfonylpiperazine (401 mg).

$^1$H-NMR(CDCl$_3$, δ):3.03-3.06(4H, m), 3.12-3.24(4H, m), 3.42-3.47(4H, m), 3.84(3H, s), 6.70-6.77(2H, m), 7.20-7.36 (5H, m). MS(m/z):396(M$^+$), 227.

Production Example 119

Production Example 2 was repeated except that 1-(4-methoxyphenyl)-4-phenethylpiperazine was replaced with 4-(2,5-difluoro-4-methoxyphenyl)-1-phenethylsulfonylpiperazine (401 mg). The resulting crude product was purified on TLC (developer, hexane: ethyl acetate=2:1) to provide 4-(2,5-difluoro-4-hydroxyphenyl)-1-phenethylsulfonylpiperazine (255 mg).

$^1$H-NMR(CDCl$_3$, δ):2.9-3.1(4H, m), 3.1-3.2(4H, m), 3.3-3.6(4H, m), 5.04(1H, br), 6.6-7.0(2H, m), 7.1-7.5(5H, m). MS(m/z):382(M$^+$), 213.

Preparation Example 1

Tablets

| Tablet: | |
|---|---|
| | mg/tablet |
| Active ingredient | 5.0 |
| Starch | 10.0 |
| Lactose | 73.0 |
| Carboxymethylcellulose-calcium | 10.0 |
| Talc | 1.0 |
| Magnesium stearate | 1.0 |
| | 100.0 |

The active ingredient is ground to a particle size not greater than 70 μm, to which starch, lactose and carboxymethylcellulose-calcium are added and mixed thoroughly. Ten (10) percent of starch paste is added to the above powdery mixture and mixed by stirring, to prepare granules. Drying the granules, their particle diameter is grained to around 1,000 μm, followed by mixing with talc and magnesium stearate and punching into tablets.

The invention claimed is:

1. A compound of the formula:

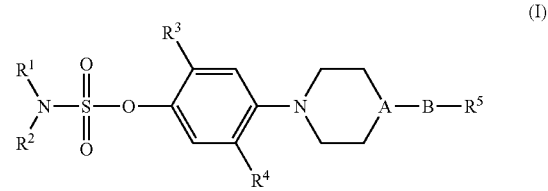

wherein

R$^1$ and R$^2$ stand for, independently from each other, hydrogen or lower alkyl, R$^3$ and R$^4$ stand for, independently from each other, hydrogen, halogen, cyano or lower alkyl, A stands for nitrogen or CH, B stands for CH$_2$, SO$_2$, CO, CH=CH or phenylene (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), and R$^5$ stands for hydrogen, straight chain or branched chain C$_1$-C$_{10}$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), benzoyl-lower alkyl (in which the phenyl moiety in the benzoyl may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl, piperidinyl-lower alkyl, phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl), benzoyl (in which the phenyl moiety in the benzoyl may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl) or amino (in which the amino may be further substituted with lower alkyl or may form cyclic amino group)

where all occurrences of "lower" above signify 1-6 carbon atoms, or a pharmaceutically acceptable salt thereof.

2. The compound or a pharmaceutically acceptable salt thereof as set forth in claim 1, in which both $R^1$ and $R^2$ stand for hydrogen atoms.

3. The compound or a pharmaceutically acceptable salt thereof as set forth in claim 1, in which $R^3$ and $R^4$ stand for, independently from each other, hydrogen or halogen.

4. The compound or a pharmaceutically acceptable salt thereof as set forth in claim 3, in which the halogen is fluorine.

5. The compound or a pharmaceutically acceptable salt thereof as set forth in claim 1, in which B stands for $CH_2$ or $SO_2$.

6. The compound or a pharmaceutically acceptable salt thereof as set forth in claim 1, in which $R^5$ stands for straight chain or branched chain $C_3$-$C_9$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl or phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl).

7. The compound or a pharmaceutically acceptable salt thereof as set forth in claim 1, in which $R^5$ stands for phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl).

8. The compound or a pharmaceutically acceptable salt thereof as set forth in claim 6, in which the straight chain or branched chain $C_3$-$C_9$ alkyl is n-butyl, n-pentyl, n-hexyl, n-heptyl, n-octyl or n-nonyl.

9. The compound or a pharmaceutically acceptable salt thereof as set forth in claim 6, in which the cycloalkyl-lower alkyl is cyclopentylmethyl, cyclopentylethyl, cyclopentyl-n-propyl, cyclopentyl-n-butyl, cyclohexylmethyl, cyclohexylethyl, cyclohexyl-n-propyl or cyclohexyl-n-butyl.

10. The compound or a pharmaceutically acceptable salt thereof as set forth in claim 7, in which the substituted phenyl is fluorophenyl or chlorophenyl.

11. A pharmaceutical preparation which comprises the compound of the formula (I) or a pharmaceutically acceptable salt thereof as set forth in claim 1 and non-toxic adjuvants.

12. Method for treating breast cancer, which comprises administering therapeutically effective amount of the compound of the formula (I) or a pharmaceutically acceptable salt thereof as set forth in claim 1.

13. The compound or a pharmaceutically acceptable salt thereof as set forth in claim 2, in which $R^3$ and $R^4$ stand for, independently from each other, hydrogen or halogen.

14. The compound or a pharmaceutically acceptable salt thereof as set forth in claim 2, in which B stands for $CH_2$ or $SO_2$.

15. The compound or a pharmaceutically acceptable salt thereof as set forth in claim 3, in which B stands for $CH_2$ or $SO_2$.

16. The compound or a pharmaceutically acceptable salt thereof as set forth in claim 4, in which B stands for $CH_2$ or $SO_2$.

17. The compound or a pharmaceutically acceptable salt thereof as set forth in claim 2, in which $R^5$ stands for straight chain or branched chain $C_3$-$C_9$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl or phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl).

18. The compound or a pharmaceutically acceptable salt thereof as set forth in claim 3, in which $R^5$ stands for straight chain or branched chain $C_3$-$C_9$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl or phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl).

19. The compound or a pharmaceutically acceptable salt thereof as set forth in claim 4, in which $R^5$ stands for straight chain or branched chain $C_3$-$C_9$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl or phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl).

20. The compound or a pharmaceutically acceptable salt thereof as set forth in claim 5, in which $R^5$ stands for straight chain or branched chain $C_3$-$C_9$ alkyl, phenyl-lower alkyl (in which the phenyl moiety may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl), cycloalkyl-lower alkyl or phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl)amino, lower alkylcarbonyl, lower alkylcarbonylamino, sulfamoylamino, and amino lower alkylcarbonyl).

21. The compound or a pharmaceutically acceptable salt thereof as set forth in claim 2, in which $R^5$ stands for phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl).

22. The compound or a pharmaceutically acceptable salt thereof as set forth in claim 3, in which $R^5$ stands for phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl).

23. The compound or a pharmaceutically acceptable salt thereof as set forth in claim 4, in which $R^5$ stands for phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl).

24. The compound or a pharmaceutically acceptable salt thereof as set forth in claim 5, in which $R^5$ stands for phenyl (which may be further substituted with 1-3 substituents selected from the group consisting of halogen, lower alkyl, hydroxy, lower alkoxy, amino, cyano, nitro, halogeno-lower alkyl, cyano-lower alkyl, lower alkylamino, di(lower alkyl) amino, lower alkylcarbonyl, lower alkylcarbonylamino, sulfamoylamino, and amino lower alkylcarbonyl).

* * * * *